United States Patent
Borrello et al.

(10) Patent No.: US 9,468,643 B2
(45) Date of Patent: Oct. 18, 2016

(54) PDE5 INHIBITOR COMPOSITIONS AND METHODS FOR IMMUNOTHERAPY

(71) Applicant: The Johns Hopkins University, Baltimore, MD (US)

(72) Inventors: Ivan M. Borrello, Baltimore, MD (US); Paolo Serafini, Miami Shores, FL (US); Kimberly A. Noonan, Baltimore, MD (US); Vincenzo Bronte, Abano Terme (IT)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 14/281,363

(22) Filed: May 19, 2014

(65) Prior Publication Data
US 2014/0255433 A1    Sep. 11, 2014

Related U.S. Application Data

(63) Continuation of application No. 11/794,855, filed as application No. PCT/US2006/000699 on Jan. 9, 2006, now abandoned.

(60) Provisional application No. 60/642,029, filed on Jan. 7, 2005.

(51) Int. Cl.
| A61K 31/519 | (2006.01) |
| A61K 31/4985 | (2006.01) |
| A61K 31/53 | (2006.01) |
| A61K 45/06 | (2006.01) |

(52) U.S. Cl.
CPC ......... *A61K 31/519* (2013.01); *A61K 31/4985* (2013.01); *A61K 31/53* (2013.01); *A61K 45/06* (2013.01)

(58) Field of Classification Search
CPC .............................................. A61K 2039/5158
See application file for complete search history.

(56) References Cited

U.S. PATENT DOCUMENTS

| 6,200,771 B1 | 3/2001 | Liu et al. |
| 6,235,776 B1 | 5/2001 | Pamukcu et al. |
| 6,359,002 B2 | 3/2002 | Pamukcu et al. |
| 6,500,610 B1 | 12/2002 | Pamukcu et al. |
| 6,555,547 B1 | 4/2003 | Pamukcu et al. |
| 6,683,080 B2* | 1/2004 | Fryburg ................. A61K 31/00 514/242 |
| 6,992,070 B2 | 1/2006 | Donahue et al. |
| 2003/0215528 A1 | 11/2003 | Graham et al. |

FOREIGN PATENT DOCUMENTS

| WO | 2003/063875 A1 | 8/2003 |
| WO | 2004/026319 A2 | 4/2004 |
| WO | 2005013937 A2 | 2/2005 |

OTHER PUBLICATIONS

Zhao et al. Circulation, 2001, vol. 104, No. 4, pp. 424-428.*
Eardley I et al. Br. J. Psychiatry, 2001, vol. 178, pp. 325-330.*
Toward T J et al.: "Effect of Phosphodiesterase-5 Inhibitor, Sildenafil (Viagra), in Animal Models of Airway Disease" American Journal of Respiratory and Critical Care Medicine 20040115 US, vol. 169, No. 2, Jan. 15, 2004 (Jan. 15, 2004), pp. 227-234, XP002550285.
Almand et al., J. Immunol., 2001, vol. 166, pp. 678-689.
Serafini et al., Cancer Immunol., Immunother., 2004, vol. 53, pp. 64-72.
Qian et al., The Journal of Urology, 2003, vol. 170, pp. 994-997.
D'Ambrosio et al., I.J. Radiation Oncology, Biology, Physics, 2003, vol. 57, No. 2, Supple., p. S274.
Goluboff et al., Urology, 1999, vol. 53, pp. 440-445.
Chan et al., Clinical Cancer Research, 2002, vol. 8, pp. 904-912.
Puszlai et al., J. Clin. Oncol., 2003, vol. 21, pp. 3454-3461.

* cited by examiner

*Primary Examiner* — James D Anderson
(74) *Attorney, Agent, or Firm* — Foley Hoag LLP

(57) ABSTRACT

The invention features methods and compositions featuring a PDE5 inhibitor for treating or preventing immunological-mediated disease in a subject.

16 Claims, 8 Drawing Sheets

PDE5 INHIBITOR COMPOSITIONS AND METHODS FOR IMMUNOTHERAPY

REFERENCE TO RELATED APPLICATIONS

This application is a continuation of U.S. patent application Ser. No. 11/794,855, filed Oct. 8, 2008, pending, which is the U.S. national stage of PCT Patent Application No. PCT/US2006/000699, filed Jan. 9, 2006, which claims the benefit of U.S. Provisional Application Ser. No. 60/642,029, filed on Jan. 7, 2005, the contents of which are incorporated herein by reference.

BACKGROUND OF THE INVENTION

Host immunity to cancers has been extensively documented both in animal models and humans (1). In fact, there is strong evidence that the immune surveillance plays a critical role in limiting tumor outgrowth in the early stages of tumorigenesis (2, 3). However, the ability to prime tumor-specific T-cells and sustain an immune response that imparts a measurable clinical benefit, is limited in the setting of an established tumor burden (4, 5). Taken together, these findings suggest numerous requirements for effective immunotherapy. Tumor-specific T cells must not only possess a sizeable precursor frequency and reach sufficient numbers following activation, but they must also be able to traffic to the tumor site and effectively kill their targets in situ.

Growing tumors are able to modify their microenvironment and render it more immunosuppressive. Such intratumoral changes include altering the cytokine milieu, changing the extracellular matrix, and recruiting immune cells with a suppressive function. In mice, the $CD11b^+/Gr1^+$ MSCs represent one population of cells within the tumor microenvironment responsible for the immunosuppression accompanying tumor growth (6, 7). Their elimination in tumor-bearing hosts restores $CD8^+$ T cell responsiveness (8, 9). This observation points to a reversible process and supports the hypothesis that strategies aimed at the pharmacologic inhibition of these pathways can be effective in restoring immune responsiveness. L-Arginine metabolism is a key pathway used by MSCs to blunt the anti-tumor response both in mice and humans ((10, 11) and Serafini, Noonan unpublished data). Arg1 and NOS2, the main enzymes that catabolize L-arginine, can, in fact, work either alone or synergistically in restrain T-cells response (12). Through an understanding of these critical suppressive pathways, it is possible to determine whether selective immunopharmacologic targeting can augment anti-tumor immunity. Nitroaspirin derivatives were recently shown to down-regulate NOS2 expression in tumor associated MSCs and to abrogate MSC-mediated immune-suppression in vivo (13) but the mechanisms of these effects were not defined. While the transcriptional and posttranscriptional mechanisms regulating NOS2 expression have been extensively studied, little is known about the pathways regulating Arginase expression.

Agents increasing intracellular cGMP levels can induce either positive or negative effects on NOS2 in a cell dependent manner (14). In macrophages, for example, cGMP analogues inhibit NOS2 expression (15). Phosphodiesterase-5 (PDE5) inhibitors such as (sildenafil (Viagra®), vardenafil (Levitra®), tadalafil (Cialis®)) increase intracellular concentrations of cGMP with therapeutic implications that include the treatment of erectile dysfunction, (16) pulmonary hypertension (17) and cardiac hypertrophy (18). The results delineated herein relate to new mechanisms and functions involving PDE inhibitors, thus providing new therapeutic compositions and methods for treating or preventing disease and disease symptoms.

SUMMARY OF THE INVENTION

The invention features methods and compositions for the treatment and prevention of disease or disease symptoms. This invention is based on the discovery that PDE5 plays an important role in immune regulation.

In one aspect, the invention generally features a method of treating or preventing disease, disease symptoms, or disease progression in a subject (e.g., a human patient). The method comprises administering to the subject an effective amount of a PDE5 inhibitor.

In another aspect, the invention provides a method of treating, preventing, reducing, or reversing cancer in a subject (e.g., a human patient), the method comprising administering to the subject an effective amount of a PDE5 inhibitor, where the administration of the inhibitor treats, prevents, reduces or reverses cancer.

In another aspect, the invention provides a method for treating, preventing, reducing, or reversing disease in a subject having or having a propensity to develop the disease, the method comprising administering to the subject an effective amount of a PDE5 inhibitor, where the inhibitor treats, prevents, reduces or reverses the disease.

In another aspect, the invention provides a composition for the treatment of a condition selected from the group consisting of cancer (e.g., multiple myeloma, melanoma, breast, stomach, head and neck, ovarian, colon, prostate, cervical cancer), chronic infection, or hematopoietic reconstitution following chemotherapy, the composition comprising a PDE5 inhibitor in a pharmaceutically acceptable excipient, where administration of the composition to a subject results in treatment of the cancer, chronic infection, or hematopoietic reconstitution following chemotherapy.

In another aspect, the invention provides a composition for the treatment of disease (e.g., any disease delineated herein), the composition comprising at least 0.1-200 mg of a PDE5 inhibitor in a pharmaceutically acceptable excipient.

In various embodiments of the above aspects, the composition comprises at least 10, 20, 100, or 150 mg of a PDE5 inhibitor. In yet other embodiments of the above aspects, the composition provides for the sustained release of the PDE5 inhibitor In still other embodiments, the composition provides for release of the PDE5 inhibitor over at least 4-8, 8-12, or 12-24 hours. In yet other embodiments of the above aspects, the composition consists essentially of a PDE5 inhibitor.

In another aspect, the invention provides pharmaceutical pack comprising a composition comprising at least 5 mg of a PDE5 inhibitor in a pharmaceutically acceptable excipient, where the pharmaceutical pack is labeled for use in the treatment or prevention of disease (e.g., any disease delineated herein).

In a related aspect, the invention provides pharmaceutical pack comprising a composition comprising at least 5 mg of a PDE5 inhibitor in a pharmaceutically acceptable excipient, where the pharmaceutical pack is labeled for use in the treatment or prevention of disease (e.g., any disease delineated herein).

In various embodiments of the previous aspects, the pack comprises at least 10 mg, 20 mg, or 100 mg of a PDE5 inhibitor. In other embodiments, the PDE5 inhibitor is provided in a sustained release formulation. In other embodiments, the composition consists essentially of a PDE5 inhibitor. In other embodiments, further comprising written instructions for administering the composition to a subject for the treatment or prevention of disease (e.g., any disease delineated herein).

DETAILED DESCRIPTION OF THE INVENTION

Definitions

Figure 1:
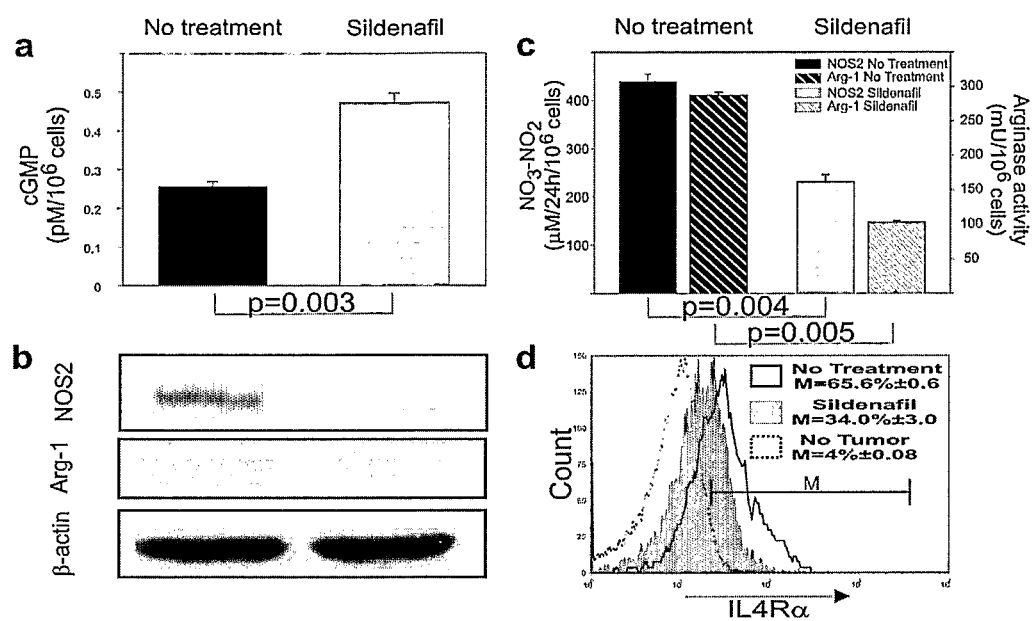
FIG. 1: In vivo PDE5 inhibition downregulates NOS2 in tumor-associated MSCs. A cohort of mice were challenged with $0.5 \times 10^6$ C26GM cells and treated (black bars) with sildenafil (20 mg/kg/day) or left untreated (gray bars). After nine days the mice were sacrificed, single cell suspensions were obtained from the tumors through collagenase treatment, and the tumor-associated CD11b$^+$ cells were magnetically purified as described in the Material and Methods. A) Intracellular concentration of cGMP was measured on the lysate of $10^6$ CD11b$^+$ cells through a competitive Enzyme ImmunoAssay (EIA) kit. B) Western blot analysis was performed to detect NOS2, Arg-1 and β-actin expression on $0.5 \times 10^6$ magnetically purified tumor-associated CD11b$^+$ cells. C) NO production was evaluated as the concentration of NO$_3$—NO$_2$ in the supernatant of $10^6$ purified CD11b$^+$ cells cultured for 24 h in DMEM. Arginase activity was determined on cell lysates and normalized for the number of cells. D) Purified tumor-derived CD11b$^+$ cells were labeled with anti CD11b-APC and anti-IL4Rα-PE. The histogram is gated on CD11b$^+$ live cells purified from either the spleen of tumor free (no tumor) mice, untreated C26GM tumor-bearing mice (no treatment) or sildenafil-treated tumor-bearing mice (Sildenafil). Data are the average+/−SD of IL4Rα$^+$ cells from two independent experiments.

By "PDE5 inhibitor" is meant a compound that inhibits cGMP hydrolysis by phosphodiesterase-5. PDE5 inhibitors preferably reduce PDE5 enzymatic activity by at least 5% (e.g., 10%, 15%, 20%, 30%, 50%, 60%, 75%, 85%, 90% or 95%). Methods for assaying the activity of a PDE5 inhibitor are known in the art and are described herein.

By "treat" is meant decrease, suppress, attenuate, diminish, arrest, or stabilize the development or progression of a disease.

By "disease" is meant any condition or disorder that damages or interferes with the normal function of a cell, tissue, or organ.

By "modulation" or "modulating" is meant any alteration (e.g., increase or decrease) in a biological function or activity.

By "reduce" or "increase" is meant alter negatively or positively, respectively, by at least 5%. An alteration may be by 5%, 10%, 25%, 30%, 50%, 75%, or even by 100%.

By "subject" is meant a mammal, such as a human patient or an animal (e.g., a rodent, bovine, equine, porcine, ovine, canine, feline, or other domestic mammal).

An "effective amount" is an amount sufficient to effect a beneficial or desired clinical result.

The term "hydrate" means a compound of the present invention or a salt thereof, which further includes a stoichiometric or non-stoichiometric amount of water bound by non-covalent intermolecular forces.

A "Marker" is any compound (e.g., molecule, protein, nucleic acid) or portion thereof (e.g., atom, functional group) or physical characteristic (e.g., radioactivity, binding, energy emission) that is measurable and whose presence, absence, or quantification is useful to provide an indication or correlation with an effect or activity. The Marker can be any characteristic or identifier, including for example, a chemical, a fluid, a protein, gene, promoter, enzyme, protein, labeled molecule, tagged molecule, antibody, and the like.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

The compounds (e.g., PDE inhibitors, additional therapeutic agents) described herein can also be any of salts, prodrugs and prodrug salts of said compound, or any solvates, hydrates and polymorphs of any of the foregoing. The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein. All crystal forms of the compounds described herein are expressly included in the present invention.

As used herein, the term "salt" or "pharmaceutically acceptable salt," is a salt formed from, for example, an acid and a basic group of a compound of any one of the formulae disclosed herein. Illustrative salts include, but are not limited to, sulfate, citrate, acetate, chloride, bromide, iodide, nitrate, bisulfate, phosphate, acid phosphate, lactate, salicylate, acid citrate, tartrate, oleate, tannate, pantothenate, bitartrate, ascorbate, succinate, maleate, besylate, fumarate, gluconate, glucaronate, saccharate, formate, benzoate, glutamate, methanesulfonate, ethanesulfonate, benzenesulfonate, and p-toluenesulfonate salts. The term "pharmaceutically acceptable salt" also refers to a salt prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl) amine; N-methyl-D-glucamine; and amino acids such as arginine, lysine, and the like. The term "pharmaceutically acceptable salt" also refers to a salt prepared from a compound of any one of the formulae disclosed herein having a basic functional group, such as an amino functional group, and a pharmaceutically acceptable inorganic or organic acid. Suitable acids include hydrogen sulfate, citric acid, acetic acid, hydrochloric acid (HCl), hydrogen bromide (HBr), hydrogen iodide (HI), nitric acid, phosphoric acid, lactic acid, salicylic acid, tartaric acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

Methods Of The Invention

The invention generally provides compositions comprising PDE5 inhibitors that are useful for the prevention or treatment of disease or disease symptoms (e.g., any disease delineated herein). Compositions and methods of the invention are particularly useful for the treatment or prevention of proliferative diseases, cancer, or tumors. This invention is based, in part, on the discoveries that PDE5 is useful for treating conditions delineated herein.

The methods herein include administering to the subject (including a subject identified as in need of such treatment) an effective amount of a compound described herein, or a composition described herein to produce a beneficial effect to the subject. Identifying a subject in need of such treatment can be in the judgment of a subject or a health care professional and can be subjective (e.g. opinion) or objective (e.g. measurable by a test or diagnostic method).

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration of a therapeutically effective amount of a compound described herein, such as a PDE5 inhibitor (e.g., vardenafil, tadalafil, or sildenafil) to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which are mediated by an immune response (e.g., anti-tumor immune response).

In aspects of the methods herein, assays are used to monitor the condition of a subject prior to, during, or following treatment with a PDE5A inhibitor. Treatments can be used in conjunction with one or more relevant diagnostic test(s) for determining the efficacy, the progression, or the appropriate dosage in the methods of the invention.

Any number of standard methods are available for assaying certain markers. Methods for assaying include any one or more of the following: tumor size, measurement, x-ray, CAT scan, magnetic resonance imaging, protein expression, nucleic acid expression, isotopologue, radiolabel, fluorescent probe, and the like.

Prophylactic and Therapeutic Applications

One aspect is a method of modulating myeloid suppressor cells (MSCs) immune suppression in a subject comprising administration to the subject of a PDE-5 inhibitor compound. Another aspect is a method of modulating arginase-1 (Arg-1) activity in a subject identified as in need of such treatment comprising administration to the subject of a PDE-5 inhibitor compound. Another aspect is a method of modulating nitric oxide synthase 2 (NOS2) activity in a subject identified as in need of such treatment comprising administration to the subject of a PDE-5 inhibitor compound. Another aspect is a method of modulating (e.g., down-regulating) interleukin-4Rα (IL-4Rα) activity in a subject identified as in need of such treatment comprising administration to the subject of a PDE-5 inhibitor compound. The methods can be wherein the modulating is down-regulation.

Another aspect is a method of modulating (e.g., activating) CD8+ T cells in a subject identified as in need of such treatment comprising administration to the subject of a PDE-5 inhibitor compound. Another aspect is a method of improving the efficacy of immune-based treatment protocols of malignancies in a subject comprising the step of further administration to the subject of a PDE-5 inhibitor compound in addition to the immune-based treatment steps.

Another aspect is a method of reducing tumor size in a subject comprising administration to the subject an effective amount of a PDE-5 inhibitor, wherein the subject is identified as in need of anti-tumor treatment with a PDE-5 inhibitor compound.

Another aspect is a method of modulating the suppressive function of Arg-1 or NOS2 in a subject comprising administration to the subject an effective amount of a PDE-5 inhibitor, wherein the subject is identified as in need of such treatment with a PDE-5 inhibitor compound.

Another aspect is a method of reducing NO production in a subject comprising administration to the subject an effective amount of a PDE-5 inhibitor, wherein the subject is identified as in need of such treatment with a PDE-5 inhibitor compound.

Another aspect is a method of modulating T-cell proliferation in a subject comprising administration to the subject an effective amount of a PDE-5 inhibitor, wherein the subject is identified as in need of such treatment with a PDE-5 inhibitor compound.

Another aspect is a method of modulating the efficacy of adoptive T-cell immunotherapy in a subject comprising administration to the T-cells an effective amount of a PDE-5 inhibitor, wherein the administration results in expansion of T cells in vitro in the presence of PDE-5 inhibitors. The PDE-5 inhibitor is thus useful as an adjuvant in adoptive cell transfer (ACT) protocols. Such pre-treatment of T-cells with a PDE-5 inhibitor can enhance the effectiveness of a therapeutic (e.g., vaccine) by modulating immunesuppression when administered to a subject, thus allowing for greater efficacy of the vaccine itself.

Another aspect is a method of modulating peripheral blood lymphocyte (PBL) proliferation in a subject comprising administration to the subject an effective amount of a PDE-5 inhibitor, wherein the subject is identified as in need of such treatment with a PDE-5 inhibitor compound.

Another aspect is a method of modulating $CD4^+$ or $CD8^+$ proliferation in a subject comprising administration to the subject an effective amount of a PDE-5 inhibitor, wherein the subject is identified as in need of such treatment with a PDE-5 inhibitor compound.

In other aspects, the compositions and methods for treating, preventing or modulating disease herein are those wherein the disease is a disease mediated by myeloid suppressor cells (MSCs). The compositions and methods for treating, preventing or modulating disease include diseases such as cancer (e.g., multiple myeloma, lymphomas, melanoma, breast, stomach, head and neck, ovarian, colon, prostate, lung, high grade gliomas, or cervical cancer), chronic infection, chronic inflammation, and hematopoietic reconstitution following chemotherapy. The methods can further comprise the step of assessing MSC levels in the subject; or can further comprise the steps of assessing MSC levels in the subject before and after administration. The assessment can be made by surface marker expression, by MSC number, or by measure of immunosuppression function.

In each of the embodiments herein, an additional therapeutic agent may be administered together with a PDE inhibitor compound of this invention as part of a single dosage form or as separate dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administering of the second therapeutic agent may occur before, concurrently with, and/or after the administering of the compound of this invention. When administration of the second therapeutic agent occurs concurrently with a compound of this invention, the two (or more) agents may be administered in a single dosage form (such as a composition of this invention comprising a compound of the invention and an second therapeutic agent as described above), or in separate dosage forms. The administration of a composition of this invention comprising both a compound of the invention and a second therapeutic agent to a subject does not preclude the separate administration of said second therapeutic agent, any other therapeutic agent or any compound of this invention to said subject at another time during a course of treatment.

Examples of additional anticancer therapeutic agents include, for example, an antiangiogenesis agent, selective estrogen-receptor modulator (SERM), breast cancer therapeutic agent, aromatase inhibitor, biologic response modifiers, hormonal therapies agent, anthracycline, taxane, alkylating agent, taxol, cis-platin, arabinofuranosyl cytosine (ara-C), 5-fluorouracil (5-FU), altretamine, busulfan, chlorambucil, cyclophosphamide, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, prednisone, bleomycin, dactinomycin, daunorubicin, doxirubicin, idarubicin, mitoxantrone, losoxantrone, mitomycin-c, plicamycin, paclitaxel, docetaxel, CPI-11, epothilones, topotecan, irinotecan, 9-amino camptothecan, 9-nitro camptothecan, GS-211, etoposide, teniposide, vinblastine, vincristine, vinorelbine, procarbazine, asparaginase, pegaspargase, methoxtrexate, octreotide, estramustine, hydroxyurea, tamoxifen, raloxifene, toremifene, exemestane, letrozole, anastrozole, megestrol, trastuzumab, goserelin acetate, fulvestrant, doxorubicin, epirubicin, or cyclophosphonamide and the like. Immunotherapeutic agents are also useful in the embodiments delineated herein. Examples of immune-based strategies include cancer-specific vaccines such as DNA-based, protein-based, whole cell tumor vaccines, dendritic cell based vaccines; adoptive T cell therapy; strategies aimed at augmenting T cell function through blockade or elimination of inhibitory or suppressor mechanisms such as CTLA-4 blockade, elimination of regulatory T cells (Tregs) or abrogation of myeloid suppressor mechanisms such as in this patent or through activation of T cells such as anti-CD3/CD28 stimulation, growth in IL-2.

PDE5 Inhibitors

PDE5 inhibitors are known in the art, and include, but are not limited to, sildenafil (Compound 1), vardenafil (Compound 2), tadalafil (Compound 3), EMD 360527, DA 8159, or analogs thereof, or any other compound that inhibits cGMP hydrolysis by phosphodiesterase-5 (PDE5).

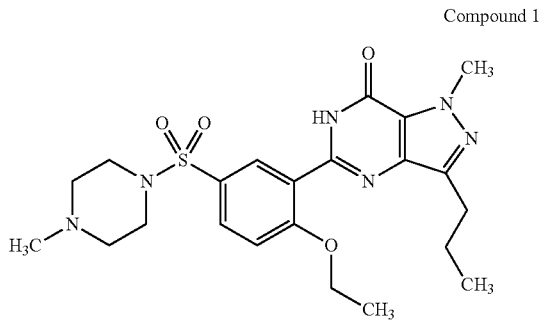

Compound 1

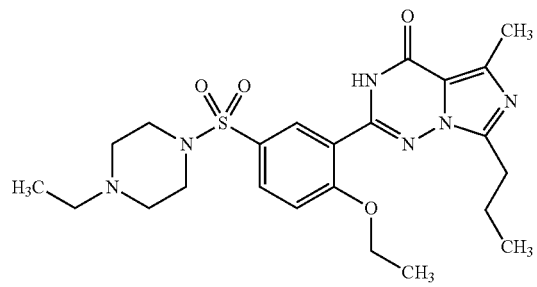

Compound 2

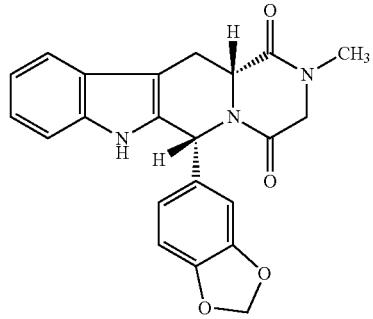

Compound 3

Certain compounds useful in the present invention can be represented by the structure (Formula I):

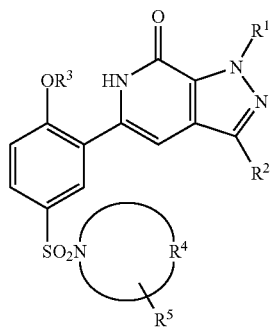

Formula I in which $R^1$ is H, $C_1$-$C_3$ alkyl, $C_3$-$C_5$ cycloalkyl or $C_1$-$C_3$ perfluoroalkyl; $R^2$ is H, $C_1$-$C_6$ alkyl optionally substituted by OH, $C_1$-$C_3$ alkoxy or $C_3$-$C_6$ cycloalkyl, or $C_1$-$C_3$ perfluoroalkyl; $R^3$ is $C_1$-$C_6$ alkyl, $C_3$-$C_6$ alkenyl, $C_3$-$C_6$ alkynyl, $C_3$-$C_{67}$ cycloalkyl, $C_1$-$C_6$ perfluoroalkyl or ($C_3$-$C_6$ cycloalkyl) $C_1$-$C_6$ alkyl; $R^4$ taken together with the nitrogen atom to which it is attached completes a 4-N—($R^6$)-piperazinyl group; $R^5$ is H, $C_1$-$C_4$ alkyl, $C_1$-$C_3$ alkoxy, $NR^7R^8$, or $CON R^7R^8$; $R^6$ is H, $C_1$-$C_6$ alkyl, ($C_1$-$C_3$ alkoxy) $C_2$-$C_6$ alkyl hydroxy $C_2$-$C_6$ alkyl, ($R^7R^8N$) $C_2$-$C_6$ alkyl, ($R^7R^8NCO$) $C_1$-$C_6$ alkyl, $CON R^7R^8$, $CSN R^7R^8$ or $C(NH)N R^7R^8$; $R^7$ and $R^8$ are each independently H, $C_1$-$C_4$ alkyl, ($C_1$-$C_3$ alkoxy) $C_2$-$C_4$ alkyl or hydroxy $C_2$-$C_4$ alkyl; and pharmaceutically acceptable salts thereof.

Other preferred compounds for use in the present invention are disclosed in U.S. Pat. No. 6,362,178 and can be represented by the structure (Formula II):

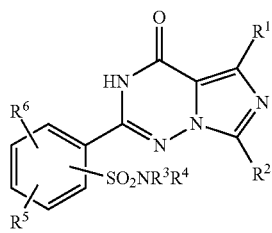

Formula II in which

R¹ represents hydrogen or straight-chain or branched alkyl having up to 4 carbon atoms, R² represents straight-chain alkyl having up to 4 carbon atoms, R³ and R⁴ are identical or different and each represents hydrogen or represents straight-chain or branched alkenyl or alkoxy having in each case up to 8 carbon atoms, or represents a straight-chain or branched alkyl chain having up to 10 carbon atoms which is optionally interrupted by an oxygen atom and which is optionally mono- or polysubstituted by identical or different substituents selected from the group consisting of trifluoromethyl, trifluoromethoxy, hydroxyl, halogen, carboxyl, benzyloxycarbonyl, straight-chain or branched alkoxycarbonyl having up to 6 carbon atoms and/or by radicals of the formulae —SO₃H, -(A)$_a$-NR⁷R⁸, —O—CO—NR⁷'R⁸', —S(O)$_b$—R⁹, —P(O)(OR¹⁰)(OR¹¹),

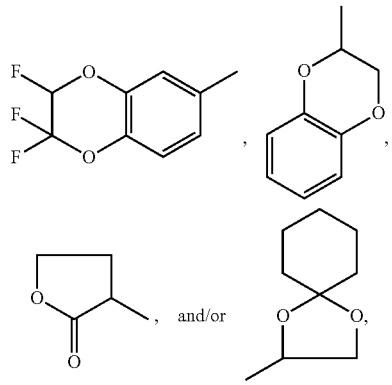

in which a and b are identical or different and each represents a number 0 or 1, A represents a radical CO or SO₂, R⁷, R⁷', R⁸ and R⁸' are identical or different and each represents hydrogen, or represents cycloalkyl having 3 to 8 carbon atoms, aryl having 6 to 10 carbon atoms, a 5- to 6-membered unsaturated, partially unsaturated or saturated, optionally benzo-fused heterocycle having up to 3 heteroatoms from the group consisting of S, N and O, where the abovementioned ring systems are optionally mono- or polysubstituted by identical or different substituents selected from the group consisting of hydroxyl, nitro, trifluoromethyl, trifluoromethoxy, carboxyl, halogen, straight-chain or branched alkoxy or alkoxycarbonyl having in each case up to 6 carbon atoms or by a group of the formula —(SO₂)$_c$—NR¹²R¹³, in which c represents a number 0 or 1, R¹² and R¹³ are identical or different and each represents hydrogen or straight-chain or branched alkyl having up to 5 carbon atoms, or R⁷, R⁷', R⁸ and R⁸' each represent straight-chain or branched alkoxy having up to 6 carbon atoms, or represents straight-chain or branched alkyl having up to 8 carbon atoms which is optionally mono- or polysubstituted by identical or different substituents selected from the group consisting of hydroxyl, halogen, aryl having 6 to 10 carbon atoms, straight-chain or branched alkoxy or alkoxycarbonyl having in each case up to 6 carbon atoms or by a group of the formula —(CO)$_d$—NR¹⁴R¹⁵, in which R¹⁴ and R¹⁵ are identical or different and each represents hydrogen or straight-chain or branched alkyl having up to 4 carbon atoms, and d represents a number 0 or 1, or R⁷ and R⁸ and/or R⁷' and R⁸' together with the nitrogen atom form a 5- to 7-membered saturated heterocycle which may optionally contain a further heteroatom from the group consisting of S and O or a radical of the formula —NR¹⁶, in which R¹⁶ represents hydrogen, aryl having 6 to 10 carbon atoms, benzyl, a 5- to 7-membered aromatic or saturated heterocycle having up to 3 heteroatoms from the group consisting of S, N and O which is optionally substituted by methyl, or represents straight-chain or branched alkyl having up to 6 carbon atoms which is optionally substituted by hydroxyl, R⁹ represents aryl having 6 to 10 carbon atoms, or represents straight-chain or branched alkyl having up to 4 carbon atoms, R¹⁰ and R¹¹ are identical or different and each represents hydrogen or straight-chain or branched alkyl having up to 4 carbon atoms, and/or the alkyl chain listed above under R³/R⁴ is optionally substituted by cycloalkyl having 3 to 8 carbon atoms, aryl having 6 to 10 carbon atoms or by a 5- to 7-membered partially unsaturated, saturated or unsaturated, optionally benzo-fused heterocycle which may contain up to 4 heteroatoms from the group consisting of S, N and O or a radical of the formula —NR¹⁷, in which R¹⁷ represents hydrogen, hydroxyl, formyl, trifluoromethyl, straight-chain or branched acyl or alkoxy having in each case up to 4 carbon atoms, or represents straight-chain or branched alkyl having up to 6 carbon atoms which is optionally mono- or polysubstituted by identical or different substituents selected from the group consisting of hydroxyl and straight-chain or branched alkoxy having up to 6 carbon atoms, and where aryl and the heterocycle are optionally mono- or polysubstituted by identical or different substituents selected from the group consisting of nitro, halogen, —SO₃H, straight-chain or branched alkyl or alkoxy having in each case up to 6 carbon atoms, hydroxyl, trifluoromethyl, trifluoromethoxy and/or by a radical of the formula —SO₂—NR¹⁸R¹⁹, in which R¹⁸ and R¹⁹ are identical or different and each represents hydrogen or straight-chain or branched alkyl having up to 6 carbon atoms, and/or R³ or R⁴ represents a group of the formula —NR²⁰R²¹, in which R²⁰ and R²¹ have the meanings of R¹⁸ and R¹⁹ given above and are identical to or different from them, and/or R³ or R⁴ represents adamantyl, or represents radicals of the formulae

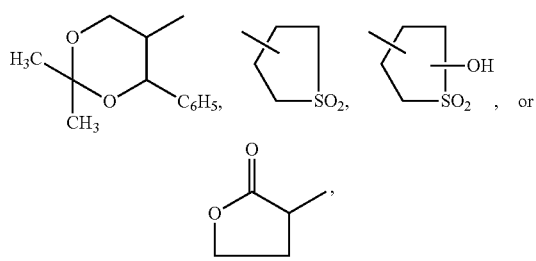

or represents cycloalkyl having 3 to 8 carbon atoms, aryl having 6 to 10 carbon atoms or represents a 5- to 7-membered partially unsaturated, saturated or unsaturated, optionally benzo-fused heterocycle which may contain up to 4 heteroatoms from the group consisting of S, N and O, or a radical of the formula —$NR^{22}$, in which $R^{22}$ has the meaning of $R^{16}$ given above and is identical to or different from it, or represents carboxyl, formyl or straight-chain or branched acyl having up to 5 carbon atoms, and where cycloalkyl, aryl and/or the heterocycle are optionally mono- or polysubstituted by identical or different substituents selected from the group consisting of halogen, triazolyl, trifluoromethyl, trifluoromethoxy, carboxyl, straight-chain or branched acyl or alkoxycarbonyl having in each case up to 6 carbon atoms, nitro and/or by groups of the formulae —$SO_3H$, —$OR^{23}$, $(SO_2)_e NR^{24}R^{25}$, —$P(O)(OR^{26})(OR^{27})$, in which e represents a number 0 or 1, $R^{23}$ represents a radical of the formula

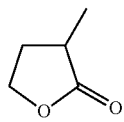

or represents cycloalkyl having 3 to 7 carbon atoms, or represents hydrogen or straight-chain or branched alkyl having up to 4 carbon atoms which is optionally substituted by cycloalkyl having 3 to 7 carbon atoms, benzyloxy, tetrahydropyranyl, tetrahydrofuranyl, straight-chain or branched alkoxy or alkoxycarbonyl having in each case up to 6 carbon atoms, carboxyl, benzyloxycarbonyl or phenyl which for its part may be mono- or polysubstituted by identical or different substituents selected from the group consisting of straight-chain or branched alkoxy having up to 4 carbon atoms, hydroxyl and halogen, and/or alkyl which is optionally substituted by radicals of the formulae —CO—$NR^{28}R^{29}$ or —CO—$R^{30}$, in which $R^{28}$ and $R^{29}$ are identical or different and each represents hydrogen or straight-chain or branched alkyl having up to 8 carbon atoms, or $R^{28}$ and $R^{29}$ together with the nitrogen atom form a 5- to 7-membered saturated heterocycle which may optionally contain a further heteroatom from the group consisting of S and O, and $R^{30}$ represents phenyl or adamantyl, $R^{24}$ and $R^{25}$ have the meanings of $R^{18}$ and $R^{19}$ given above and are identical to or different from them, $R^{26}$ and $R^{27}$ have the meanings of $R^{10}$ and $R^{11}$ given above and are identical to or different from them and/or cycloalkyl, aryl and/or the heterocycle are optionally substituted by straight-chain or branched alkyl having up to 6 carbon atoms which is optionally substituted by hydroxyl, carboxyl, by a 5- to 7-membered heterocycle having up to 3 heteroatoms from the group consisting of S, N and O, or by groups of the formula —$SO_2$—$R^{31}$, $P(O)(OR^{32})(OR^{33})$ or —$NR^{34}R^{35}$, in which $R^{31}$ represents hydrogen or has the meaning of $R^9$ given above and is identical to or different from it, $R^{32}$ and $R^{33}$ have the meanings of $R^{10}$ and $R^{11}$ given above and are identical to or different from them, $R^{34}$ and $R^{35}$ are identical or different and each represents hydrogen or straight-chain or branched alkyl having up to 6 carbon atoms which is optionally substituted by hydroxyl or by straight-chain or branched alkoxy having up to 4 carbon atoms, or $R^{34}$ and $R^{35}$ together with the nitrogen atom form a 5- to 6-membered saturated heterocycle which may contain a further heteroatom from the group consisting of S and O, or a radical of the formula —$NR^{36}$, in which $R^{36}$ represents hydrogen, hydroxyl, straight-chain or branched alkoxycarbonyl having up to 7 carbon atoms or straight-chain or branched alkyl having up to 5 carbon atoms which is optionally substituted by hydroxyl, or $R^3$ and $R^4$ together with the nitrogen atom form a 5- to 7-membered unsaturated or saturated or partially unsaturated, optionally benzo-fused heterocycle which may optionally contain up to 3 heteroatoms from the group consisting of S, N and O, or a radical of the formula —$NR^{37}$, in which $R^{37}$ represents hydrogen, hydroxyl, formyl, trifluoromethyl, straight-chain or branched acyl, alkoxy or alkoxycarbonyl having in each case up to 4 carbon atoms, or represents straight-chain or branched alkyl having up to 6 carbon atoms which is optionally mono- or polysubstituted by identical or different substituents selected from the group consisting of hydroxyl, trifluoromethyl, carboxyl, straight-chain or branched alkoxy or alkoxycarbonyl having in each case up to 6 carbon atoms, or by groups of the formula -$(D)_f NR^{38}R^{39}$, —CO—$(CH_2)_g$—O—CO—$R^{40}$, —CO—$(CH_2)_h$—$OR^{41}$ or —$P(O)(OR^{42})(OR^{43})$, in which g and h are identical or different and each represents a number 1, 2, 3 or 4, and f represents a number 0 or 1, D represents a group of the formula —CO or —$SO_2$, $R^{38}$ and $R^{39}$ are identical or different and each has the meaning of $R^7$ and $R^8$ given above, $R^{40}$ represents straight-chain or branched alkyl having up to 6 carbon atoms, $R^{41}$ represents straight-chain or branched alkyl having up to 6 carbon atoms, $R^{42}$ and $R^{43}$ are identical or different and each represents hydrogen or straight-chain or branched alkyl having up to 4 carbon atoms, or $R^{37}$ represents a radical of the formula —$(CO)_i$-E, in which i represents a number 0 or 1, E represents cycloalkyl having 3 to 7 carbon atoms or benzyl, represents aryl having 6 to 10 carbon atoms or a 5- to 6-membered aromatic heterocycle having up to 4 heteroatoms from the group consisting of S, N and O, where the abovementioned ring systems are optionally mono- or polysubstituted by identical or different constituents selected from the group consisting of nitro, halogen, —$SO_3H$, straight-chain or branched alkoxy having up to 6 carbon atoms, hydroxyl, trifluoromethyl, trifluoromethoxy, or by a radical of the formula —$SO_2$—$NR^{44}R^{45}$, in which $R^{44}$ and $R^{45}$ have the meaning of $R^{18}$ and $R^{19}$ given above and are identical to or different from them, or E represents radicals of the formulae

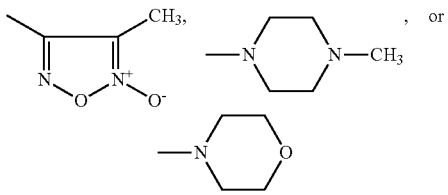

and the heterocycle listed under $R^3$ and $R^4$, which is formed together with the nitrogen atom, is optionally mono- or polysubstituted, if appropriate also geminally, by identical or different substituents selected from the group consisting of hydroxyl, formyl, carboxyl, straight-chain or branched acyl or alkoxycarbonyl having in each case up to 6 carbon atoms, nitro and groups of the formulae —$P(O)(OR^{46})(OR^{47})$,

=$NR^{48}$, or —$C(O)_jNR^{49}R^{50}$,
in which $R^{46}$ and $R^{47}$ have the meanings of $R^{10}$ and $R^{11}$ given above and are identical to or different from them, $R^{48}$ represents hydroxyl or straight-chain or branched alkoxy having up to 4 carbon atoms, j represents a number 0 or 1, and $R^{49}$ and $R^{50}$ are identical or different and have the meanings of $R^{14}$ and $R^{15}$ given above, and/or the heterocycle listed under $R^3$ and $R^4$, which is formed together with the nitrogen atom, is optionally substituted by straight-chain or branched alkyl having up to 6 carbon atoms which is optionally mono- or polysubstituted by identical or different substituents selected from the group consisting of hydroxyl, halogen, carboxyl, cycloalkyl or cycloalkyloxy having in each case 3 to 8 carbon atoms, straight-chain or branched alkoxy or alkoxycarbonyl having in each case up to 6 carbon atoms, or by a radical of the formula —$SO_3H$, —$NR^{51}R^{52}$ or $P(O)OR^{53}OR^{54}$, in which $R^{51}$ and $R^{52}$ are identical or different and each represents hydrogen, phenyl, carboxyl, benzyl or straight-chain or branched alkyl or alkoxy having in each case up to 6 carbon atoms, $R^{53}$ and $R^{54}$ are identical or different and have the meanings of $R^{10}$ and $R^{11}$ given above, and/or the alkyl is optionally substituted by aryl having 6 to 10 carbon atoms which for its part may be mono- or polysubstituted by identical or different substituents selected from the group consisting of halogen, hydroxyl, straight-chain or branched alkoxy having up to 6 carbon atoms, or by a group of the formula —$NR^{51'}R^{52'}$, in which $R^{51'}$ and $R^{52'}$ have the meanings of $R^{51}$ and $R^{52}$ given above and are identical to or different from them, and/or the heterocycle listed under $R^3$ and $R^4$, which is formed together with the nitrogen atom, is optionally substituted by aryl having 6 to 10 carbon atoms or by a 5- to 7-membered saturated, partially unsaturated or unsaturated heterocycle having up to 3 heteroatoms from the group consisting of S, N and O, optionally also attached via a nitrogen function, where the ring systems for their part may be substituted by hydroxyl or by straight-chain or branched alkyl or alkoxy having in each case up to 6 carbon atoms, or $R^3$ and $R^4$ together with the nitrogen atom form radicals of the formulae

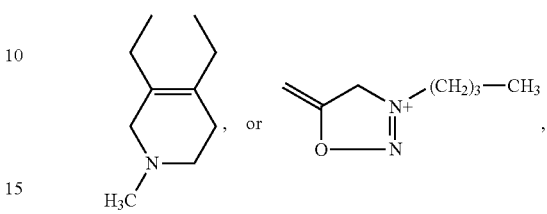

$R^5$ and $R^6$ are identical or different and each represents hydrogen, straight-chain or branched alkyl having up to 6 carbon atoms, hydroxyl or represents straight-chain or branched alkoxy having up to 6 carbon atoms, and their salts, hydrates, N-oxides and structural isomers.

Other suitable compounds include those of the following Formula III:

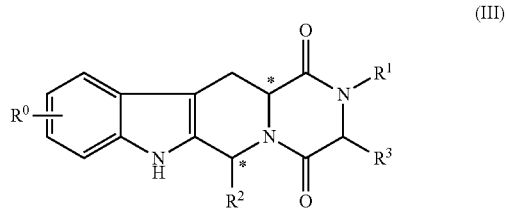

wherein in Formula III, $R^0$ represents hydrogen, halogen, or $C_{1-6}$ alkyl;

$R^1$ represents hydrogen, $C_{1-6}$ alkyl, $C_{2-6}$ alkenyl, $C_{2-6}$ alkynyl, halo$C_{1-6}$ alkyl, $C_{3-8}$ cycloalkyl, $C_{3-8}$ cycloalkyl$C_{1-3}$ alkyl, aryl$C_{1-3}$ alkyl, or heteroaryl$C_{1-3}$ alkyl;

$R^2$ represents an optionally substituted monocyclic aromatic ring selected from benzene, thiophene, furan, and pyridine, or an optionally substituted bicyclic ring;

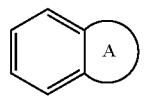

attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulphur, and nitrogen; and $R^3$ represents hydrogen of $C_{1-3}$ alkyl, or $R^1$ and $R^3$ together represent a 3- or 4-membered alkyl or alkenyl chain; and pharmaceutically and salts and solvates (e.g., hydrates) thereof.

Certain preferred compounds also include those of the following Formula IV:

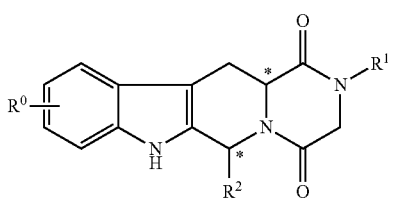

(IV)

wherein in Formula IV, R⁰ represents hydrogen, halogen, or $C_{1-6}$ alkyl;

$R^1$ represents hydrogen, $C_{1-6}$ alkyl, halo$C_{1-6}$ alkyl, $C_{3-8}$ cycloalkyl$C_{1-3}$ alkyl, aryl$C_{1-3}$ alkyl, or heteroaryl$C_{1-3}$ alkyl; and $R^2$ represents an optionally substituted monocyclic aromatic ring selected from benzene, thiophene, furan, and pyridine, or an optionally substituted bicyclic ring

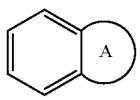

attached to the rest of the molecule via one of the benzene ring carbon atoms, and wherein the fused ring A is a 5- or 6-membered ring which can be saturated or partially or fully unsaturated and comprises carbon atoms and optionally one or two heteroatoms selected from oxygen, sulphur, and nitrogen; and pharmaceutically acceptable salts and solvates (e.g., hydrates) thereof.

A further group of compounds preferred for use in the invention are compounds of the following Formula V:

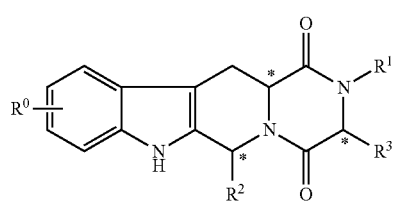

(V)

wherein in Formula V:
$R^0$ represents hydrogen, halogen, or $C_{1-6}$ alkyl;
$R^1$ represents hydrogen or $C_{1-6}$ alkyl;
$R^2$ represents the bicyclic ring

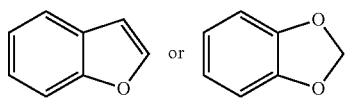

which can be optionally substituted by one or more groups selected from halogen and $C_{1-3}$ alkyl; and $R^3$ represents hydrogen or $C_{1-3}$ alkyl; and pharmaceutically acceptable salts and solvates (e.g., hydrates) thereof.

In Formula IV above, with respect to $R^1$, the term "aryl" as part of an aryl$C_{1-3}$ alkyl group means phenyl or phenyl substituted by one or more (e.g., 1, 2, or 3) substituents selected from halogen, $C_{1-6}$ alkyl, $C_{1-6}$ alkoxy, and methylenedioxy. The term "heteroaryl" as part of a heteroaryl$C_{1-3}$ alkyl group means thienyl, furyl, or pyridyl, each optionally substituted by one or more (e.g., 1, 2, or 3) substituents selected from halogen, $C_{1-6}$ alkyl, and $C_{1-6}$ alkoxy. The term "$C_{3-8}$ cycloalkyl" as a group or part of a $C_{3-8}$ cycloalkyl$C_{1-3}$ alkyl group means a monocyclic ring comprising three to eight carbon atoms. Examples of suitable cycloalkyl rings include the $C_{3-6}$ cycloalkyl rings cyclopropyl, cyclobutyl, cyclopentyl, and cyclohexyl.

In formula IV above, with respect to $R^2$, optional benzene ring substituents are selected from one or more (e.g., 1, 2, or 3) atoms or groups comprising halogen, hydroxy, $C_{1-6}$ alkyl, $C_{1-6}$ alkoxy, $CO_2R^b$, halo$C_{1-6}$ alkyl, halo$C_{1-6}$ alkoxy, cyano, nitro, and $NR^aR^b$, where $R^a$ and $R^b$ are each hydrogen or $C_{1-6}$ alkyl, or $R^a$ also can represent $C_{2-7}$ alkanoyl or $C_{1-6}$ alkylsulphonyl. Optional substituents for the remaining ring systems are selected from one or more (e.g., 1, 2, or 3 atoms or groups comprising halogen, $C_{1-6}$ alkyl, $C_{1-6}$ alkoxy, and aryl$C_{1-3}$ alkyl as defined above. The bicyclic ring

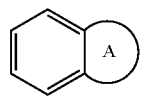

can, for example, represent naphthalene, a heterocycle such as benzoxazole, benzothiazole, benzisoxazole, benzimidazole, quinoline, indole, benzothiophene, benzofuran, or

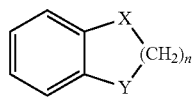

wherein n is an integer 1 or 2 and X and Y each can represent $CH_2$, O, S, or NH.

See also U.S. Pat. Nos. 6,916,927, 6,911,542, 6,903,099, 6,878,711, 6,872,721, 6,858,620, 6,825,197, 6,774,128, 6,723,719, 6,699,870, 6,670,366, 5,859,006 and 5,250,534. Other PDE5 inhibitors useful in the methods of the invention are described in WO 03/063875; WO 03/1012761 WO 2004/037183, and WO 98/38168. All of these patents and patent applications are incorporated herein by reference in their entirety.

Sildenafil is commercially available in three dosages of 25, 50, or 100 mg and has an $IC_{50}$ of approximately 10 nM. Effective plasma concentrations are between 1 nM and 250 nM, where the bottom of the range is any integer between 1 and 249; and the top of the range is any integer between 2 nM and 250 nM. Preferably, an effective plasma concentration is between 5 nM and 100 nM, more preferably it is between 10 nM and 50 nM (e.g., 15 nM, 20 nM, 25 nM, 30 nM, 40 nM, or 45 nM).

Tadalafil is commercially available in three dosages of 5, 10, or 20 mg and has an $IC_{50}$ of approximately 1 nM. Following oral administration of a 20 mg dose of tadalafil to healthy subjects, tadalafil is rapidly absorbed with the peak plasma concentration of 378 ng/ml occurring two hours post-dose. Preferably an effective plasma concentration is between 5 nM and 100 nM, more preferably it is between 10 nM and 50 nM (e.g., 15 nM, 20 nM, 25 nM, 30 nM, 40 nM, or 45 nM). Tadalafil has a relative large apparent volume of distribution (Vd/F) of 62.6 L, and a low apparent oral clearance (CL/F) of 2.48 L/h. As a result, the mean elimination half-life of tadalafil is about 17.5 h, which is substantially longer than that of sildenafil or vardenafil.

Vardenafil is commercially available in three dosages of 5 mg, 10 mg, and 20 mg and has an $IC_{50}$ of 0.7 nM. Effective plasma concentrations of vardenafil are between 0.1 and 5.0 nM.

The skilled artisan appreciates that any compound that reduces the activity of PDE5 is useful in the methods of the invention. Other exemplary compounds useful in the methods of the invention include UK-343,664 (Walker et al., Xenobiotica, 31: 651-664), UK-427,387, UK-357903 [1-ethyl-4-{3-[3-ethyl-6,7-dihydro-7-oxo-2-(2-pyridylmethyl)-2H-pyrazolo[4,3-d]pyrimidin-5-yl]-2-(2-methoxyethoxy)-5-pyridylsulphonyl}piperazine] (Gardiner et al. *J Pharmacol Exp Ther.* 2005; 312: 265-271), UK-371800 (Pfizer), UK-313794 (Pfizer) and UK-343664 (Abel et al., Xenobiotica. 2001 31:665-76); TA-1790 from Tanabe Seiyaku; CP-248, CP-461 and exisulind (Deguchi et al., Molecular Cancer Therapeutics 803-809, 2002), which are available from Osi Pharmaceuticals; pyrazolinone; EMD82639 (4-(4-[2-ethyl-phenylamino)-methylene]-3-methyl-5-oxo-4,5-di-hydro-pyrazol-1-yl)-benzoic acid (Senzaki et al., FASEB Journal. 2001; 15:1718-1726); [7-(3-Chloro-4-methoxy-benzylamino)-1-methyl-3-propyl-1H-pyrazolo[4,3-d]pyrimidin-5-ylmethoxy]-acetic acid (EMD360527), 4-[4-(3-Chloro-4-methoxy-benzylamino)-benzo[4,5]thieno[2,3-d]-pyrimidin-2-yl]-cyclohexanecarboxylic acid, ethanolamin salt (EMD221829) and 5-[4-(3-Chloro-4-methoxy-benzylamino)-5,6,7,8-tetrahydro-benzo[4,5]thieno[2,3-d]pyrimidin-2-yl]-pentanoic acid (EMD171827), which are commercially available from Merck KgaA (Darmstadt, Del.) and are described, for example, in Scutt et al. (BMC Pharmacol. 2004; 4: 10); 3-(1-Methyl-7-oxo-3-propyl-6,7-dihydro-1H-pyrazolo-[4,3-d]pyrimidin-5-yl)-N-[2-(1-methylpyrrolidin-2-yl)ethyl]-4-propoxybenzenesulfonamide (DA-8259); E-4021 (Dukarm et al., Am. J. Respir. Crit. Care Med., 1999, 160:858-865); pentoxifylline and FR22934 (Fujisawa).

The synthesized compounds can be separated from a reaction mixture and further purified by a method such as column chromatography, high pressure liquid chromatography, or recrystallization. As can be appreciated by the skilled artisan, methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* 2nd. Ed., Wiley-VCH Publishers (1999); T. W. Greene and P. G. M. Wuts, *Protective Groups in Organic Synthesis,* 3rd. Ed., John Wiley and Sons (1999); L. Fieser and M. Fieser, *Fieser and Fieser's Reagents for Organic Synthesis*, John Wiley and Sons (1999); and L. Paquette, ed., *Encyclopedia of Reagents for Organic Synthesis*, John Wiley and Sons (1995), and subsequent editions thereof.

Pharmaceutical Compositions

The present invention features pharmaceutical preparations comprising a PDE5 inhibitor (e.g., sildenafil, vardenafil, tadalafil, or analogs thereof) together with pharmaceutically acceptable carriers, where the compounds provide for the treatment of disease or disease symptoms (e.g., cancer, any disease delineated herein). Pharmaceutical preparations of the invention have both therapeutic and prophylactic applications. In one embodiment, a pharmaceutical composition includes an effective amount of a PDE5 inhibitor. The compositions should be sterile and contain a therapeutically effective amount of a PDE5 inhibitor in a unit of weight or volume suitable for administration to a subject (e.g., a human patient). The compositions and combinations of the invention can be part of a pharmaceutical pack, where the PDE5 inhibitor is present in individual dosage amounts.

Pharmaceutical compositions of the invention to be used for prophylactic or therapeutic administration should be sterile. Sterility is readily accomplished by filtration through sterile filtration membranes (e.g., 0.2 µm membranes), by gamma irradiation, or any other suitable means known to those skilled in the art. Therapeutic compositions generally are placed into a container having a sterile access port, for example, an intravenous solution bag or vial having a stopper pierceable by a hypodermic injection needle. These compositions ordinarily will be stored in unit or multi-dose containers, for example, sealed ampoules or vials, as an aqueous solution or as a lyophilized formulation for reconstitution.

A PDE5 inhibitor may be combined, optionally, with a pharmaceutically acceptable excipient. The term "pharmaceutically-acceptable excipient" as used herein means one or more compatible solid or liquid filler, diluents or encapsulating substances that are suitable for administration into a human. The term "carrier" denotes an organic or inorganic ingredient, natural or synthetic, with which the active ingredient is combined to facilitate administration. The components of the pharmaceutical compositions also are capable of being co-mingled with a PDE5 inhibitor of the present invention, and with each other, in a manner such that there is no interaction that would substantially impair the desired pharmaceutical efficacy.

Compounds of the present invention can be contained in a pharmaceutically acceptable excipient. The excipient preferably contains minor amounts of additives such as substances that enhance isotonicity and chemical stability. Such materials are non-toxic to recipients at the dosages and concentrations employed, and include buffers such as phosphate, citrate, succinate, acetate, lactate, tartrate, and other organic acids or their salts; tris-hydroxymethylaminomethane (TRIS), bicarbonate, carbonate, and other organic bases and their salts; antioxidants, such as ascorbic acid; low molecular weight (for example, less than about ten residues) polypeptides, e.g., polyarginine, polylysine, polyglutamate and polyaspartate; proteins, such as serum albumin, gelatin, or immunoglobulins; hydrophilic polymers, such as polyvinylpyrrolidone (PVP), polypropylene glycols (PPGs), and polyethylene glycols (PEGs); amino acids, such as glycine, glutamic acid, aspartic acid, histidine, lysine, or arginine; monosaccharides, disaccharides, and other carbohydrates including cellulose or its derivatives, glucose, mannose, sucrose, dextrins or sulfated carbohydrate derivatives, such as heparin, chondroitin sulfate or dextran sulfate; polyvalent metal ions, such as divalent metal ions including calcium ions, magnesium ions and manganese ions; chelating agents, such as ethylenediamine tetraacetic acid (EDTA); sugar alcohols, such as mannitol or sorbitol; counterions, such as sodium or ammonium; and/or nonionic surfactants, such as polysorbates or poloxamers. Other additives may be included, such as stabilizers, anti-microbials, inert gases, fluid and nutrient replenishers (i.e., Ringer's dextrose), electrolyte replenishers, and the like, which can be present in conventional amounts.

The compositions, as described above, can be administered in effective amounts. The effective amount will depend upon the mode of administration, the particular condition being treated and the desired outcome. It may also depend upon the stage of the condition, the age and physical condition of the subject, the nature of concurrent therapy, if any, and like factors well known to the medical practitioner. For therapeutic applications, it is that amount sufficient to achieve a medically desirable result.

With respect to a subject having a disease or disorder delineated herein, an effective amount is an amount sufficient to stabilize, slow, or reduce a symptom associated with the condition. Generally, doses of the compounds of the present invention would be from about 0.01 mg/kg per day to about 1000 mg/kg per day. In one embodiment, 25, 50, 75, 100, 125, 150 or 200 mg of a PDE5 inhibitor, such as sildenafil, is administered to a subject. Preferably, 100 mg of a PDE5 inhibitor is administered. Effective doses range from 0.1 nM to 200 nM, where the bottom of the range is any integer between 1 and 199, and the top of the range is any integer between 2 and 200. It is expected that doses ranging from about 5 to about 2000 mg/kg will be suitable— depending on the specific PDE5 inhibitor used. Lower doses will result from certain forms of administration, such as intravenous administration and pharmaceutical. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of a composition of the present invention.

A variety of administration routes are available. The methods of the invention, generally speaking, may be practiced using any mode of administration that is medically acceptable, meaning any mode that produces effective levels of the active compounds without causing clinically unacceptable adverse effects. In one preferred embodiment, a composition of the invention is administered orally. Other modes of administration include rectal, topical, intraocular, buccal, intravaginal, intracisternal, intracerebroventricular, intratracheal, nasal, transdermal, within/on implants, or parenteral routes or possibly intratumorally. The term "parenteral" includes subcutaneous, intrathecal, intravenous, intramuscular, intraperitoneal, or infusion. Intravenous or intramuscular routes are not particularly suitable for long-term therapy and prophylaxis. They could, however, be preferred in emergency situations. Compositions comprising a composition of the invention can be added to a physiological fluid, such as blood. Oral administration can be preferred for prophylactic treatment because of the convenience to the patient as well as the dosing schedule.

Pharmaceutical compositions of the invention can comprise one or more pH buffering compounds to maintain the pH of the formulation at a predetermined level that reflects physiological pH, such as in the range of about 5.0 to about 8.0. The pH buffering compound used in the aqueous liquid formulation can be an amino acid or mixture of amino acids, such as histidine or a mixture of amino acids such as histidine and glycine. Alternatively, the pH buffering compound is preferably an agent which maintains the pH of the formulation at a predetermined level, such as in the range of about 5.0 to about 8.0, and which does not chelate calcium ions. Illustrative examples of such pH buffering compounds include, but are not limited to, imidazole and acetate ions. The pH buffering compound may be present in any amount suitable to maintain the pH of the formulation at a predetermined level.

Pharmaceutical compositions of the invention can also contain one or more osmotic modulating agents, i.e., a compound that modulates the osmotic properties (e.g, tonicity, osmolality and/or osmotic pressure) of the formulation to a level that is acceptable to the blood stream and blood cells of recipient individuals. The osmotic modulating agent can be an agent that does not chelate calcium ions. The osmotic modulating agent can be any compound known or available to those skilled in the art that modulates the osmotic properties of the formulation. One skilled in the art may empirically determine the suitability of a given osmotic modulating agent for use in the inventive formulation. Illustrative examples of suitable types of osmotic modulating agents include, but are not limited to: salts, such as sodium chloride and sodium acetate; sugars, such as sucrose, dextrose, and mannitol; amino acids, such as glycine; and mixtures of one or more of these agents and/or types of agents. The osmotic modulating agent(s) may be present in any concentration sufficient to modulate the osmotic properties of the formulation.

Pharmaceutical compositions of the invention can also be a non-aqueous liquid formulation. Any suitable non-aqueous liquid may be employed, provided that it provides stability to the active agents (s) contained therein. Preferably, the non-aqueous liquid is a hydrophilic liquid. Illustrative examples of suitable non-aqueous liquids include: glycerol; dimethyl sulfoxide (DMSO); polydimethylsiloxane (PMS); ethylene glycols, such as ethylene glycol, diethylene glycol, triethylene glycol, polyethylene glycol ("PEG") 200, PEG 300, and PEG 400; and propylene glycols, such as dipropylene glycol, tripropylene glycol, polypropylene glycol ("PPG") 425, PPG 725, PPG 1000, PPG 2000, PPG 3000 and PPG 4000.

Pharmaceutical compositions of the invention can also be a mixed aqueous/non-aqueous liquid formulation. Any suitable non-aqueous liquid formulation, such as those described above, can be employed along with any aqueous liquid formulation, such as those described above, provided that the mixed aqueous/non-aqueous liquid formulation provides stability to the compound contained therein. Preferably, the non-aqueous liquid in such a formulation is a hydrophilic liquid. Illustrative examples of suitable non-aqueous liquids include: glycerol; DMSO; PMS; ethylene glycols, such as PEG 200, PEG 300, and PEG 400; and propylene glycols, such as PPG 425, PPG 725, PPG 1000, PPG 2000, PPG 3000 and PPG 4000.

Suitable stable formulations can permit storage of the active agents in a frozen or an unfrozen liquid state. Stable liquid formulations can be stored at a temperature of at least −70° C., but can also be stored at higher temperatures of at least 0° C., or between about 0.1° C. and about 42° C., depending on the properties of the composition.

Other delivery systems can include time-release, delayed release or sustained release delivery systems. Such systems can avoid repeated administrations of compositions of the invention, increasing convenience to the subject and the physician. Many types of release delivery systems are available and known to those of ordinary skill in the art. They include polymer base systems such as polylactides (U.S. Pat. No. 3,773,919; European Patent No. 58,481), poly(lactide-glycolide), copolyoxalates, polycaprolactones, polyesteramides, polyorthoesters, polyhydroxybutyric acids, such as poly-D-(−)-3-hydroxybutyric acid (European Patent No. 133, 988), copolymers of L-glutamic acid and gamma-ethyl-L-glutamate (Sidman, K. R. et al., Biopolymers 22: 547-556), poly (2-hydroxyethyl methacrylate) or ethylene vinyl acetate (Langer, R. et al., J. Biomed. Mater. Res. 15:267-277; Langer, R. Chem. Tech. 12:98-105), and polyanhydrides.

Other examples of sustained-release compositions include semi-permeable polymer matrices in the form of shaped articles, e.g., films, or microcapsules. Delivery systems also include non-polymer systems that are: lipids including sterols such as cholesterol, cholesterol esters and fatty acids or neutral fats such as mono- di- and tri-glycerides; hydrogel release systems such as biologically-derived bioresorbable hydrogel (i.e., chitin hydrogels or chitosan hydrogels); sylastic systems; peptide based systems; wax coatings; compressed tablets using conventional binders and excipients; partially fused implants; and the like. Specific examples include, but are not limited to: (a) erosional systems in which the agent is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480.

Another type of delivery system that can be used with the methods and compositions of the invention is a colloidal dispersion system. Colloidal dispersion systems include lipid-based systems including oil-in-water emulsions, micelles, mixed micelles, and liposomes. Liposomes are artificial membrane vessels, which are useful as a delivery vector in vivo or in vitro.

Liposomes can be targeted to a particular tissue by coupling the liposome to a specific ligand such as a monoclonal antibody, sugar, glycolipid, or protein. Liposomes are commercially available from Gibco BRL, for example, as LIPOFECTIN™ and LIPOFECTACE™, which are formed of cationic lipids such as N-[1-(2,3 dioleyloxy)-propyl]-N, N, N-trimethylammonium chloride (DOTMA) and dimethyl dioctadecylammonium bromide (DDAB). Methods for making liposomes are well known in the art and have been described in many publications, for example, in DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Liposomes also have been reviewed by Gregoriadis, G., Trends Biotechnol., 3: 235-241).

Another type of vehicle is a biocompatible microparticle or implant that is suitable for implantation into a mammalian recipient. Exemplary bioerodible implants that are useful in accordance with this method are described in PCT International application no. PCT/US/03307 (Publication No. WO 95/24929, entitled "Polymeric Gene Delivery System"). PCT/US/0307 describes biocompatible, preferably biodegradable polymeric matrices for containing an exogenous gene under the control of an appropriate promoter. The polymeric matrices can be used to achieve sustained release of the exogenous gene or gene product in the subject.

The polymeric matrix preferably is in the form of a microparticle such as a microsphere (wherein an agent is dispersed throughout a solid polymeric matrix) or a microcapsule (wherein an agent is stored in the core of a polymeric shell). Microcapsules of the foregoing polymers containing drugs are described in, for example, U.S. Pat. No. 5,075,109. Other forms of the polymeric matrix for containing an agent include films, coatings, gels, implants, and stents. The size and composition of the polymeric matrix device is selected to result in favorable release kinetics in the tissue into which the matrix is introduced. The size of the polymeric matrix further is selected according to the method of delivery that is to be used. Preferably, when an aerosol route is used the polymeric matrix and composition are encompassed in a surfactant vehicle. The polymeric matrix composition can be selected to have both favorable degradation rates and also to be formed of a material, which is a bioadhesive, to further increase the effectiveness of transfer. The matrix composition also can be selected not to degrade, but rather to release by diffusion over an extended period of time. The delivery system can also be a biocompatible microsphere that is suitable for local, site-specific delivery. Such microspheres are disclosed in Chickering, D. E., et al., Biotechnol. Bioeng., 52: 96-101; Mathiowitz, E., et al., Nature 386: 410-414.

Both non-biodegradable and biodegradable polymeric matrices can be used to deliver the compositions of the invention to the subject. Such polymers may be natural or synthetic polymers. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene, polyvinylpyrrolidone, and polymers of lactic acid and glycolic acid, polyanhydrides, poly(ortho)esters, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Methods of Treatment

In one embodiment, the present invention provides a method of inhibiting an anti-tumor immune response mediated pathway target in a subject comprising the step of administering to the subject an effective amount of a PDE5 inhibitor, preferably as part of a composition additionally comprising a pharmaceutically acceptable carrier. Preferably this method is employed to treat a subject suffering from or susceptible to a condition selected from a disease or disease symptom (e.g., cancer, tumor, any disease or disorder delineated herein). Other embodiments include any of the methods herein wherein the subject is identified as in need of the indicated treatment.

In another aspect, the method further includes administration of an additional therapeutic agent. The additional therapeutic agent can be an anticancer agent, an anti-infective, or a PDE inhibitor.

Another aspect of the invention is a compound herein (e.g., PDE inhibitor, compound of any of the formulae herein) for use in the treatment or prevention in a subject of a disease, disorder or symptom thereof delineated herein. Another aspect of the invention is the use of a PDE5 inhibitor in the manufacture of a medicament for a disease or disease symptom (e.g., cancer, tumor, any disease or disorder delineated herein) in a subject. Preferably, the medicament is used for treatment or prevention in a subject of a disease, disorder or symptom set forth above.

Kits

The invention provides kits for the treatment or prevention of a condition associated with a disease or disease symptom (e.g., cancer, tumor, anti-tumor immune response, any disease or disorder delineated herein). In one embodiment, the kit includes a pharmaceutical pack comprising an effective amount of a PDE5 inhibitor (e.g., a PDE5a inhibitor, such as sildenafil). Preferably, the compositions are present in unit dosage form. In some embodiments, the kit comprises a sterile container which contains a therapeutic or prophylactic composition; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired compositions of the invention or combinations thereof are provided together with instructions for administering them to a subject having or at risk of developing a disease or disease symptom (e.g., cancer, tumor, anti-tumor immune response, any disease or disorder delineated herein). The instructions will generally include information about the use of the compounds for the treatment or prevention of a disease or disease symptom (e.g., cancer, tumor, anti-tumor immune response, any disease or disorder delineated herein). In other embodiments, the instructions include at least one of the following: description of the compound or combination of compounds; dosage schedule and administration for treatment of a disease or disease symptom (e.g., cancer, tumor, anti-tumor immune response, any disease or disorder delineated herein); precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

Here, it is demonstrated that PDE5 blockade represents a pharmacologic target capable of down-regulating both Arg1 and NOS2 in tumor infiltrating MSCs. This down-regulation abrogates tumor induced MSCs mediated immunosuppression and enhances tumor-specific immunity that results in measurable anti-tumor activity.

This is the first demonstration that blocking MSC-mediated immunosuppression via PDE5 inhibition imparts a measurable anti-tumor immune effect. It is shown that PDE5-blockade increases intracellular cGMP resulting in degradation of NOS2 and suppression of NO production. Furthermore it also results in down-regulation of the IL4Rα-ARG-1 pathway. Thus it targets both pathways critical to MSC function. These findings establish a new role for PDE5 inhibition as a viable and effective immunological adjunct in the treatment of various malignancies adding to its therapeutic applications that already include the treatment of erectile dysfunction, pulmonary hypertension (35, 36) and cardiac hypertrophy (18).

Although NO production from tumor-associated macrophages has both tumor-promoting and tumoricidal properties, the ultimate effect of these free radicals is complex and likely dependent upon their local concentration within the microenvironment. In fact, NO exerts its tumoricidal action through modulation of p53 expression (37). Interestingly, in a model in which human cancer cells were modified to express high levels of NO, cells containing wild type p53 demonstrated reduced tumor growth whereas cells with mutant p53 showed increased production of vascular endothelial growth factor (VEGF), neovascularization and increased tumor growth (38). These studies demonstrate the duality of NO-mediated effects and its regulation by p53 within a tumor setting. Unfortunately, most human tumors possess p53 mutations (39) making them resistant to NO-mediated apoptosis. Furthermore, prolonged exposure to NO leads to the selection of a more aggressive p53 mutant clone better able to escape the tumoricidal action (40). The clinical importance of NO-mediated antitumor efficacy is further limited by the fact that many human tumors such as melanoma, breast, stomach, ovarian and cervical cancers actually express NOS2. In fact, NO can promote cancer growth not only in the early stages of tumor progression by facilitating DNA mutations (40) but also in the later stages by increasing tumor angiogenesis (41) and immunosuppression (42). With regards to the immune escape mechanisms, it has been shown that MSCs and/or tumor associated macrophages induce apoptosis or anergy in $CD8^+$ and $CD4^+$ T cells through a NOS2-dependent mechanisms (7, 20, 43). In fact, through inhibition of IL-2 signaling (20), NO production anergizes Th1 T-cells. Alternatively, in a mixed Th1-Th2 environment where arginase-induced pathways also mediate immunosuppression, MSCs produce NO and super-oxide radicals to generate peroxynitrites that induce apoptosis of activated $CD8^+$ T cells (12). With the growing understanding of the role of MSCs in tumor-induced immune dysfunction (6, 44, 45), targeted pharmacologic interventions have significant appeal in overcoming the suppressive mechanisms in immune-based therapeutic settings. It is recently shown that nitroaspirin could abrogate the inhibitory activity of NO. It restored immune responsiveness in tumor-bearing hosts and enhanced the preventive and therapeutic efficacy of antitumor vaccines (13). However, despite its use as a vaccine adjuvant, nitroaspirin demonstrated no anti-tumor efficacy when used alone.

PDE5 inhibition represents a novel immunopharmacologic target that down-modulates the expression of both Arg1 and NOS2 in MSCs. Interestingly, this approach more effectively reverses MSC-induced immune suppression than does nitroaspirin by exerting a significant in vivo anti-tumor effect. The augmented anti-tumor effect can be attributed to the ability of PDE5 inhibition to target the various suppressive pathways by which MSCs inhibit T-cell function. To our knowledge, this is the first demonstration that abrogation of MSC suppressive mechanisms alone is sufficient to generate an antitumor immune response. The measurable anti-tumor efficacy seen with PDE5 inhibitors but not with NO inhibitors is likely due to the multi-target inhibition exerted by these agents. Although results herein show that PDE5 inhibitors affect both Arg-1 and NOS2 pathways in MSCs, it is possible that additional as yet undefined pathways capable of further abrogating MSC-mediated immunosuppression may also be involved. For example, cGMP is also capable of reducing VEGF production within the hypoxic intra-tumoral environment (46).

One likely mechanism for the effect of PDE5-inhibitors on reducing NO production involves the impact of these inhibitors on mRNA stability. cGMP destabilizes NOS2 mRNA by reducing the ubiquitous mRNA binding protein, human-antigen-R (HuR) (47). HuR binds to AU-rich elements in the 3'-untranslated region (UTR) thereby increasing the mRNA half-life (48). As such, destabilization of NOS2 mRNA via PDE5 inhibition would abrogate NO-mediated immunosuppression more effectively than would competitive inhibition of NO itself.

Figure 4:
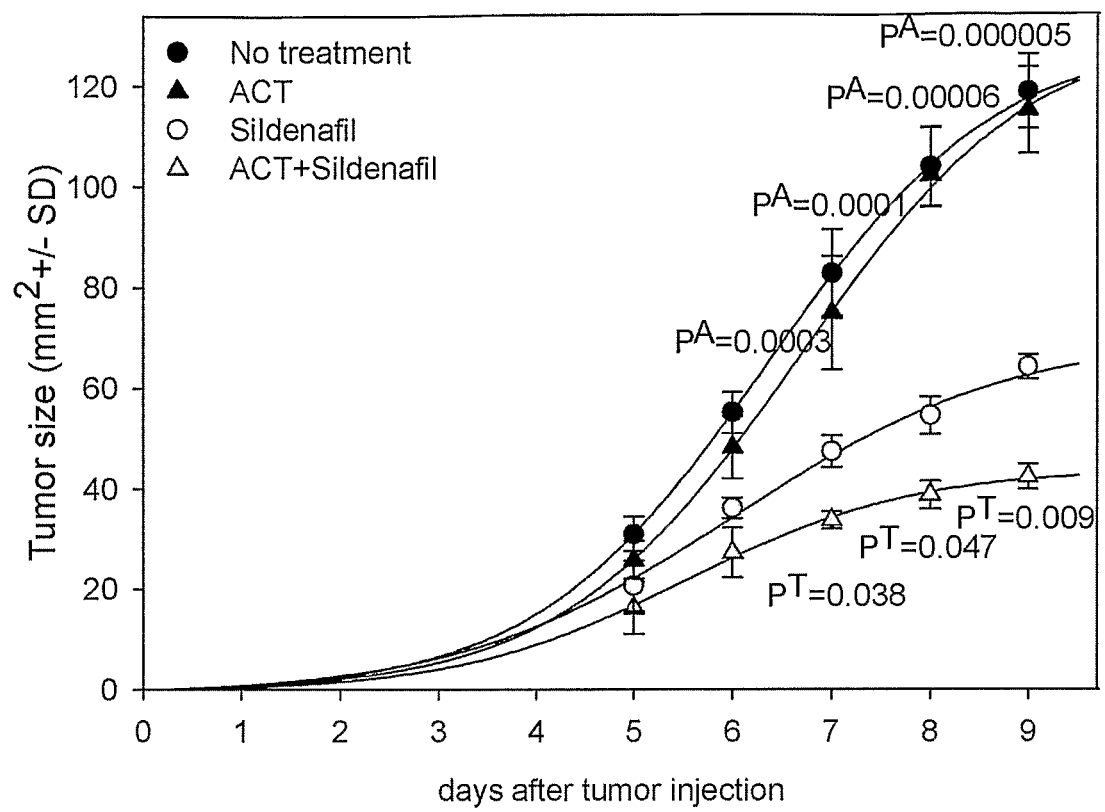
FIG. 4: Adoptive cell transfer (ACT) efficacy is improved by sildenafil treatment. BALB/c mice were challenged on day 0 with $0.5 \times 10^6$ C26GM cells s.c. and were either given sildenafil (20 mg/kg/day) in their drinking water or left untreated. Where indicated, the mice received $20 \times 10^6$ splenocytes from mice vaccinated 7 days before with $10^6$ γ-irradiated C26GM. Tumor size is indicated as the product of the two main perpendicular diameters measured with a caliper. One way Anova P value ($P^4$) is reported, The paired T-test (P value=$P^T$) was used to compare sildenafil vs sildenafil+ACT groups.
Figure 7:
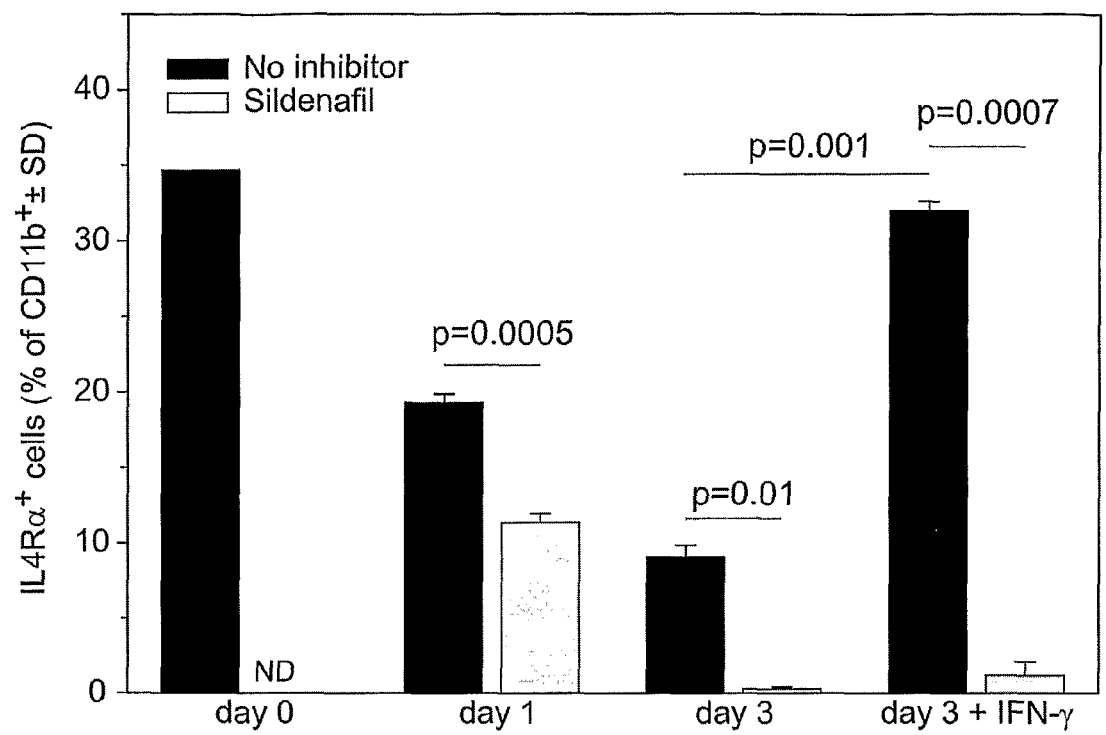
FIG. 7: Sildenafil down-regulates IL4Rα expression on purified MSCs. CD11b+ cells were magnetically purified and cultured in media with or without Sildenafil (50 μg/ml). Where indicated, INF-γ (25 ng/ml) was added on day 2. The cells were harvested at the indicated time, labeled with anti-CD11b and anti IL4Rα antibodies. The percentage of IL-4Rα$^+$ cells was determined by flow cytometry collecting 10000 CD11b$^+$ cells. 7AAD and annexin V were used to exclude dead cells. Results are expressed as the average of triplicate wells+/−the standard deviation.

Since Arg1 mRNA does not possess AU rich elements nor has it been described to be stabilized by HUR, other mechanism(s) are likely involved in PDE5-mediated down-regulation of Arg1. One possible explanation is that high levels of cGMP induced by PDE5 blockade reduce the cytosolic Ca2+ concentration (49) leading to a reduction of the calcium-dependent protein kinase C (PKC) activity (50) that in turn prevents up-regulation of IL4Rα (51). The link between IL4Rα and Arg-1 in MSCs is supported by recent data demonstrating a direct correlation between ARG1 expression and IL4Rα expression. LysM$^{Cre}$IL4Rα$^{-/flox}$ mice in which IL4Rα expression is knocked-out in neutrophils and macrophages subsequently challenged with C26GM completely rejected the tumor when adoptively transferred with tumor-primed CD8+ T cells (Gallina et al. manuscript submitted). These data support our findings by demonstrating that PDE5 blockade down-regulates IL4Rα expression on tumor-infiltrating MSCs (FIG. 1) and synergizes with the adoptive transfer of tumor-primed CD8+ T cells (FIG. 4). This effect appears to specifically target MSCs since IL4Rα expression on isolated CD11b+ cells from tumor-bearing mice is significantly reduced when co-cultured in the presence of sildenafil. Furthermore, the addition of IFN-γ, which in vivo up-regulates IL4Rα expression through both autocrine and paracrine (presumably through activated T cells) mechanisms, is significantly reduced in the presence of sildenafil (FIG. 7). Taken together these data underscore the critical role of the IL4Rα-ARG1 pathway in MSCs as well as the use of PDE5 inhibitors as therapeutically effective drugs to overcome tumor-induced immunosuppression.

Effective adoptive cellular therapy requires T cells with the predetermined antigen specificity to be present in sufficient numbers, traffic to the tumor site, and kill their target. Most solid tumors are characterized by a lymphocytic infiltration that is frequently unable to kill autologous tumor cells, indicating T cell anergy (52, 53), the presence of regulatory T cells (Tregs) (54) or the existence of a non-T cell immunosuppressive population. It was recently shown that human prostate cancer anergic TILs can be reactivated in vitro through the inhibition of NOS2 and Arg1. These findings underscore importance of MSC-mediated immunosuppression and identify putative targets of immunosuppressive pathways used by MSCs to improve immune-based therapeutic outcomes (11). These results are indicated by our in vivo studies whereby the sildenafil treatment led to an increase in intratumoral CD8+ T cell infiltration that inversely correlated with tumor size (FIG. 5b), increased the percentage of activated T cells (FIG. 5c, and d) and was the only condition in which adoptive cell transfer resulted in a measurable anti-tumor effect (FIG. 4).

The phenotype of human MSCs is still not well defined. However, there is evidence to suggest that a non-lymphoid CD34+ population plays a role in the hypo-responsiveness of PBLs from head and neck cancer patients (55). A similar unresponsiveness is seen in PBLs from multiple myeloma patients (56). While the low proliferative capacity may be due to intrinsic T cell defects, a likely explanation for T cell unresponsiveness is the presence of a non-lymphoid suppressor accessory population since PDE5-inhibition augments the proliferative index of lymphocytes from unfractionated peripheral mononuclear cell population but not of purified CD3+ cells (data not shown). Moreover, results from our experiments suggest a prominent role of both Arginase and NOS2 in MM PBLs unresponsiveness. The ability of sildenafil to restore CD3/CD28-stimulated proliferation of PBLs from both head and neck and myeloma patients suggests that the mechanisms found in mice are also present in humans.

Although different drugs such L-NMMA, Nor-NOHA, NO-aspirin, or Vitamin D3 (57) have been used in vitro and in mouse models to alter the MSCs suppressive mechanisms, they have either not been extensively tested in humans or found to be extremely toxic, as in the case with L-NMMA (58). Moreover the cytokines present in tumor microenvironment can be very different among patient and tumor stage (59) and thus can promote different suppressive pathways on MSCs. The use of safe and extensively tested PDE5 inhibitors such as sildenafil, tadalafil, or vardenafil to overcome the different MSCs immune suppressive pathways is demonstrated by results described herein.

The following examples are provided to illustrate the invention, not to limit it. Those skilled in the art will understand that the specific constructions provided below may be changed in numerous ways, consistent with the above described invention while retaining the critical properties of the compounds or combinations thereof.

EXAMPLES

PDE5 Inhibition Down-Regulates NOS2 Expression in Tumor-Associated MSCs

The primary property of MSCs is their ability to suppress an immune response. While this phenotype is an essential defining feature, emerging data reveals varying degrees of immunosuppression of MSCs isolated from different organs. Tumor-associated MSCs express greater levels of NOS2 and Arg-1 than do splenic MSCs and, thus, result in greater immune suppression (data not shown). Since cGMP analogues can reduce NO generation in monocytes (15), this investigation sought to determine whether NO production in tumor-associated MSCs could be reduced with the in vivo treatment of the PDE5 inhibitor, sildenafil (20 mg/kgday). BALB/c mice were challenged subcutaneously with the colon carcinoma, CT26WT. Half the mice were then treated with sildenafil. The mice were sacrificed 15 days later and intratumoral MSCs were purified from the single cell suspensions. MSCs derived from the sildenafil group showed higher intracellular cGMP levels than the control group as assessed by a competitive enzyme immune assay (FIG. 1a). No significant differences were seen in the non-MSC population (data not shown). Interestingly, higher cGMP concentrations correlated with down-regulation of NOS2 (FIG. 1b) and lower NO production (FIG. 1c) by the intratumoral MSCs. Surprisingly, sildenafil treatment also down-regulated Arg-1 (FIG. 1b,c) the other gene involved in MSC mediated immunosuppression. Arg-1 expression is mainly regulated by the STAT6-IL4Rα pathway (19) and data by Gallina et al. recently correlated IL4Rα expression on CD11b/GR1 with the immunosuppressive phenotype (manuscript submitted). IL4Rα expression via flow cytometry on purified tumor infiltrating MSCs from untreated or sildenafil treated mice was analyzed. IL4Rα is up-regulated in tumor infiltrating MSCs as compared to splenic MSCs from tumor free mice. In contrast, sildenafil treatment significantly reduced IL4Rα expression on the intratumoral MSCs and this correlated directly with the decrease in Arg-1 expression and activity. In addition to confirming the role of IL4Rα in MSC mediated immunosuppression, its expression in splenic MSCs cultured alone or in presence of sildenafil (FIG. 7) was analyzed. Sildenafil not only down-regulates IL4Rα in cultured MSCs, but also prevents IFN-γ mediated IL4Rα up-regulation—a necessary process for MSC-mediated immune suppression (Gallina et al. submitted). These findings reveal a novel mechanism by which MSCs suppressive pathways can be pharmacologically regulated both in vivo and in vitro: PDE5 inhibition up-regulates intracellular cGMP and decreases NOS2 and Arg1 protein levels—the mediators of MSC suppression.

In Vitro PDE5 Inhibition Abrogates MSC Immunosuppression.

Figure 2:
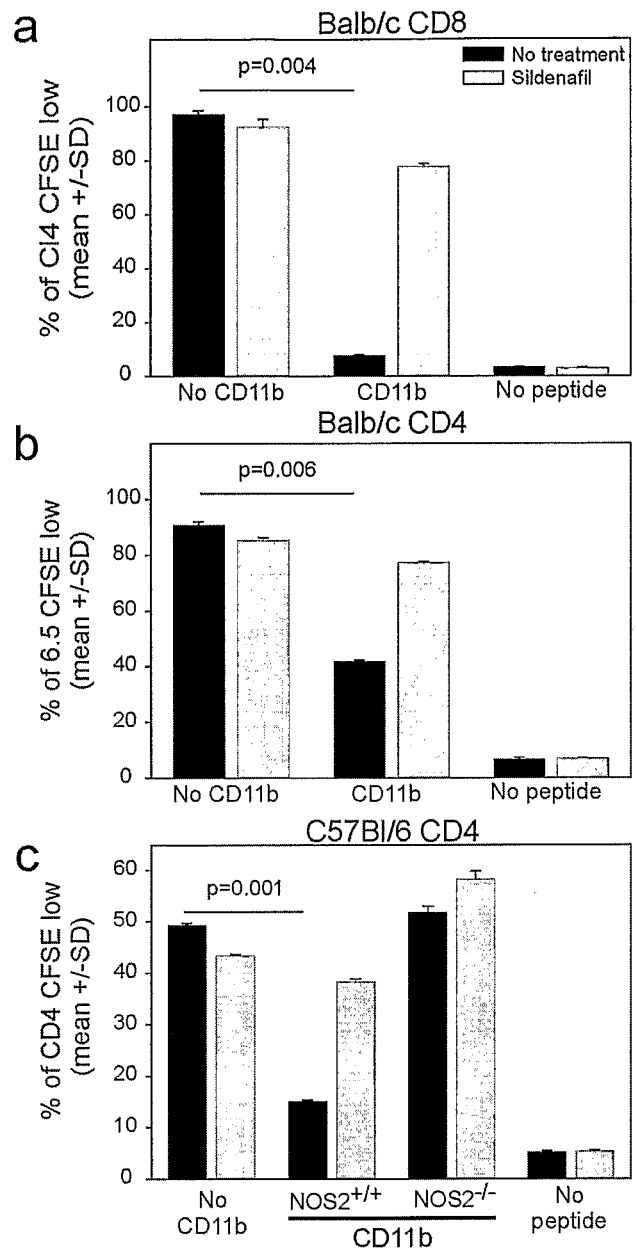
FIG. 2: PDE5 inhibition reverts MSC suppressive pathways. Splenic CD11b$^+$ cells were magnetically purified from BALB/c mice challenged 9 days before with C26GM, and added to CFSE labeled splenocytes containing either naïve HA-specific CD8$^+$ CL4 cells (A) or naïve HA specific CD4$^+$6.5 cells (B). The cultures were stimulated for 4 days with the relevant peptide in the presence or in the absence of sildenafil (50 μg/ml). The proliferation was evaluated as CFSE dilution by cytoflorimetric analysis. C) Splenic CD11b$^+$ cells were magnetically purified from C57Bl/6 NOS$^{+/+}$ or from C57Bl/6 NOS$^{-/-}$ challenged with the melanoma B 16GM 15 days before and added to CFSE labeled splenocytes containing naïve OVA specific CD4$^+$ T cells. The cultures were stimulated for 4 days with the relevant peptide in the presence or in the absence of sildenafil (50 μg/ml). The proliferation was evaluated as CFSE dilution by flow cytometry. Data derived from one of two independent experiments with similar results.

Freshly isolated MSCs from tumor-bearing mice suppress the in vitro proliferation of activated lymphocytes. The exact mechanisms of suppression appear to be strain specific: in the Th-1 prone strain, C57Bl/6, it is mediated by NOS2 through NO production (via the NOS2 catalytic domain) (20). Whereas, in the mixed Th-1/Th2 Balb/c strain, suppression is mediated either by peroxynitrite formation (via Arg1 and NOS2 co-expression) (10) or by L-arginine depletion secondary to Arg1 over-expression (21). By reducing both Arg1 and NOS2 expression, PDE5 inhibition affects all these suppressive pathways resulting in reduced MSC-mediated immunosuppression and enhances antigen-specific T cell responsiveness. Tumor-derived CD11b$^+$ MSCs were isolated from BALB/c mice bearing the colon carcinoma, C26-GM. We utilized the irradiated, C26 cell line retrovirally transduced to produce GM-CSF since this cytokine has been shown to recruit MSCs more rapidly than the unmodified CT26 cell line (10, 22, 23). We tested MSC suppressive activity by admixing MSCs with CFSE-labeled hemagluttinin (HA)-specific CD8$^+$ (clone 4) or CD4$^+$ (6.5) T cells pulsed with their relevant peptide in the presence or absence of sildenafil (FIGS. 2a and b). Whereas the addition of tumor-derived MSCs significantly impaired antigen specific T cell proliferation as demonstrated by the low percentage of CFSE$^{lo}$ clonotypic T cells, sildenafil almost completely restored both CD4$^+$ and CD8$^+$ responsiveness of antigen-specific T cells. The absence of a sildenafil-mediated enhancement in T cell function in the groups lacking CD11b cells underscores the targeted role of sildenafil on the MSC population. In an effort to understand the in vivo mechanisms mediating this effect, we utilized C57Bl/6 mice for several reasons: 1) in this strain, inhibition of NOS2 is sufficient to revert MSCs mediated immunosuppression (7); and 2) NOS2$^{-/-}$ mice are available thus enabling us to examine the effect of PDE5 blockade in the NO-mediated pathway of immunosuppression. CD11b$^+$ MSCs were isolated from either B16GM melanoma-bearing C57BL/6-NOS2$^{+/+}$ or B16GM melanoma-bearing C57BL/6-NOS2$^{-/-}$ mice. A suppression assay was performed by stimulating OVA-specific CD4$^+$ T-cells with the relevant peptide in the presence or absence of MSCs derived from either NOS2$^{+/+}$ or NOS2$^{-/-}$ mice (FIG. 2c). While the addition of C57Bl/6-NOS2$^{+/+}$-derived MSCs induced considerable T cell suppression, no suppression was observed with MSCs from NOS2$^{-/-}$ mice. Furthermore, while PDE5 inhibition reversed MSC suppression in NOS2$^{+/+}$ mice, the addition of sildenafil to the NOS2$^{-/-}$-derived MSC suppression assay did not augment T cell responsiveness. Taken together, these results confirm the role of NOS2 in MSC-mediated T cell suppression (FIG. 2c) and demonstrate that PDE5 inhibition can revert two different suppressive pathways (Arg1 and NOS2) by which MSCs impair immune responsiveness.

In Vivo PDE5 Inhibition Delays Tumor Outgrowth by an Immune Mediated Mechanism.

Figure 3:
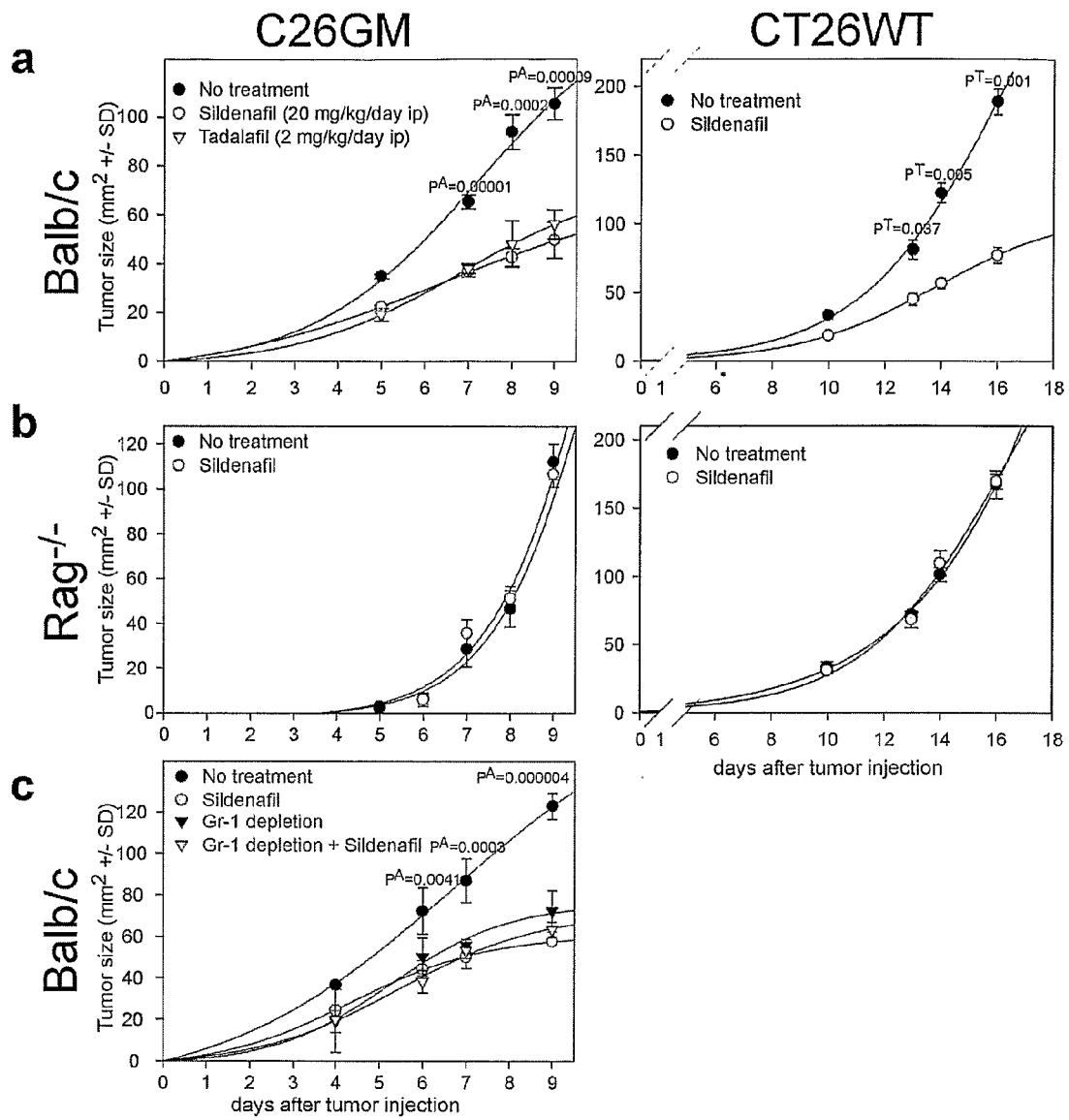
FIG. 3: PDE5 inhibition alone imparts a measurable immune-system mediated antitumor effect. Balb/c (A) or BALB/c Rag$^{-/-}$ mice (B) were challenged s.c. with $0.5 \times 10^6$ cells of the indicated tumor. Sildenafil (20 mg/kg/day) was added to the drinking water or given i.p. daily where indicated. Tadalafil (2 mg/kg/day) was given ip. Tumor size is indicated as the product of the two main perpendicular diameters measured with a caliper. (C) GR-1$^+$ cells were depleted where indicated by i.p. injection of 200 μg of anti-GR-1 depleting antibody (clone RB6-8C5.3) on day 0, 3, 6 after tumor challenge. Best fit of the data was obtained by four parameter sigmoid curves. Paired T test P value ($P^T$) or one way Anova pValue ($P^4$) are reported.
Figure 8:
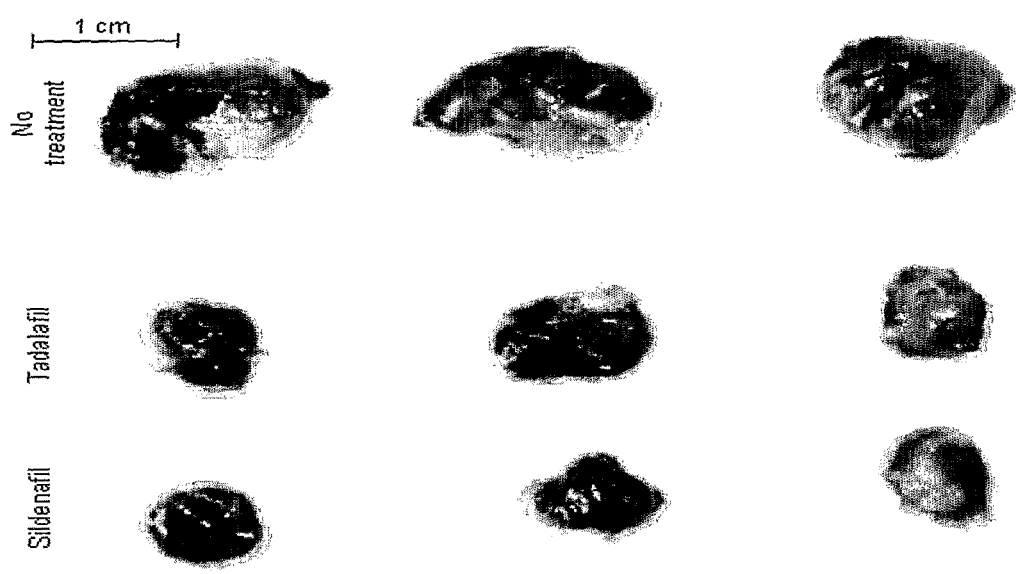
FIG. 8: PDE-5 inhibitors reduce tumor growth. Balb/c mice were challenged s.c. with $0.5 \times 10^6$ C26GM cells. Sildenafil (20 mg/kg/day), tadalafil (2 mg/kg/day) or PBS were given i.p daily. The tumors were surgically removed and photographed on day 9.

Having recently shown that the in vivo inhibition of the MSC suppressive pathways by nitro-aspirin was ineffective as a single agent but augmented the anti-tumor efficacy of vaccines on established tumors (13), it was sought to determine whether PDE5 inhibition alone, by affecting both Arg-1 and NOS2 suppressive activity, could impart a measurable anti-tumor effect. Mice were challenged either with CT26-WT or with the more aggressive tumor, C26GM and then treated with PDE5 inhibitors. As shown in FIG. 3a and FIG. 8, sildenafil or tadalafil treatment alone significantly delayed tumor outgrowth through an immune mediated mechanism as evidenced by the lack of anti-tumor efficacy in the immune deficient Rag$^{-/-}$ mice (FIG. 3b). However, the combination of PDE inhibition with the MSC-depleting anti-GR-1$^+$ antibody conferred no synergistic effect (FIG. 3c). Taken together, these data confirm that MSC-mediated immunosuppressive pathways function via NOS2-Arg1 enzymatic activity produced by GR-1$^+$ cells and demonstrate the ability of PDE5 inhibition to abrogate their activity in vivo. To the best of our knowledge, this is the first demonstration that a direct anti-tumor effect can be obtained through the pharmacologic inhibition of tumor-induced immunosuppressive pathways.

PDE5 Inhibition Enhances Anti-Tumor Efficacy of Adoptive Immunotherapy.

Adoptive immunotherapy of tumor-specific T cells offers much promise as a therapeutic modality. Considerable progress has been made in developing strategies to isolate, expand and activate tumor specific cells in vitro. In the appropriate environment, these lymphocytes can mediate significant tumor destruction. However, the mere presence of tumor reactive T cells in the peripheral circulation is not sufficient to induce tumor rejection (24). T cells must also traffic to the tumor site and overcome the intrinsic immunosuppressive barriers to effectively kill in situ. To determine whether sildenafil inhibition of the MSC suppressive pathways could improve the efficacy of adoptive immunotherapy, 20×10$^6$ C26GM-primed splenocytes were transferred into C26GM bearing animals. Following adoptive transfer, the mice were either treated with sildenafil or left untreated. As shown in FIG. 4, adoptive transfer alone demonstrated no anti-tumor efficacy whereas PDE5 inhibition showed a statistically significant reduction in tumor outgrowth. However, coupling adoptive immunotherapy with PDE5 inhibition yielded the greatest anti-tumor efficacy. These data suggest that disruption of the MSC-mediated, immunosuppressive microenvironment is critical to augment the therapeutic efficacy of adoptive immunotherapy in cancer-bearing hosts.

PDE5 Inhibition Increases the Number of Tumor Infiltrating CD8$^+$ Cells.

Figure 5:
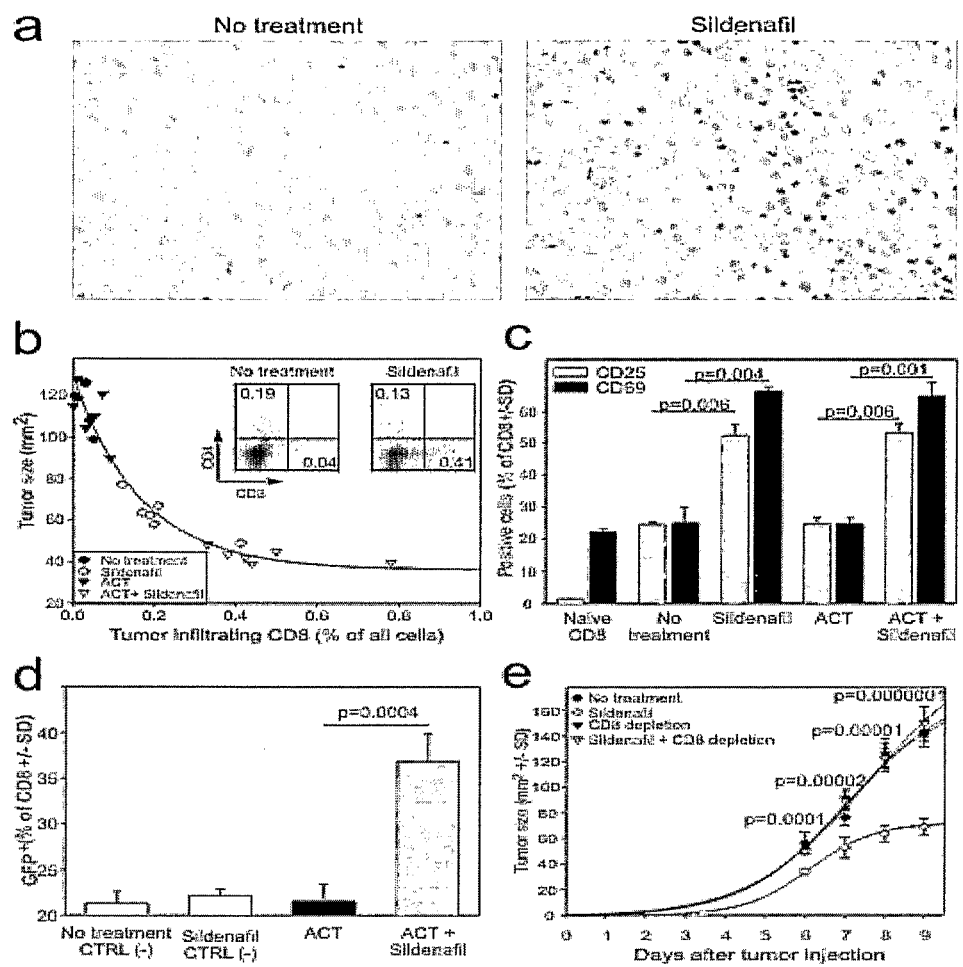
FIG. 5: PDE5 inhibition improves the infiltration and activation of tumor specific CD8$^+$ T cells A) BALB/c mice were challenged s.c. with $0.5 \times 10^6$ CT26WT cells and given sildenafil (20 mg/kg/day) in the drinking water or not. The mice were sacrificed 15 days later. The tumors were surgically removed, fixed with 10% neutral buffered formalin, and stained with hematoxylin-eosin. B) BALB/c mice were challenged with $0.5 \times 10^6$ C26GM cells s.c. Half of these mice were treated with sildenafil starting on day 0. Where indicated, adoptive transfer was performed utilizing $20 \times 10^6$ splenocytes from H2$^d$ pIL-2/GFP mice vaccinated s.c. one week earlier with γ-irradiated C26GM. After 9 days the tumors were surgically removed, treated with collagenase, labeled with anti-CD4 and anti-CD8 antibodies and analyzed by flow cytometry. The percentage of CD8$^+$ T cells was plotted against the tumor size at the time of tumor harvest. Sigma plot was used to fit a 3 parameters exponential decay curve ($y=36.13+92xe^{-5.93x}$). Pearson bivariate correlation: P=0.0000002. Data derived from 3 independent experiments. Tumor single cells suspension were also labeled with anti-CD25 or anti-CD69 antibodies (C). Data are expressed as percentage of positive cells gated on the CD8$^+$ population. D) Since the splenocytes used for the ACT were derived from pIL-2/GFP transgenic mice, IL-2 production in the C26GM-vaccinated T cells is reported as percent of GFP positive, CD8$^+$ T cells. Data are derived from two independent experiments. Paired T test P value is reported. E) BALB/c mice were challenged with $0.5 \times 10^6$ C26GM cells on day 0. Where indicated the mice were treated with either sildenafil, the anti-CD8$^+$ depleting antibody (clone 2.43) on day 0, 2, 4, and 6, or both treatments. One way Anova P value is reported. Data is reported from one of two similar experiments.

Tumor specific T-cells must be present in sufficient numbers and capable of trafficking to their targets to exert a measurable antitumor effect. In fact, a direct correlation exists between the number of infiltrating lymphocytes and a favorable clinical outcome in patients with metastatic ovarian cancer (25). Moreover, the presence and the functionality of tumor infiltrating lymphocytes (TILs) correlates with a favorable prognosis in various human malignancies (25-29). Since PDE5 inhibition augments anti-tumor immunity, whether sildenafil treatment altered the number and/or the activation state of TILs was considered. Hematoxylin-eosin staining revealed a greater intratumoral cellular infiltration in the sildenafil-treated mice compared to the untreated controls (FIG. 5a). To better evaluate these differences, tumor-bearing mice either received tumor-primed T cells or no T cells followed by sildenafil treatment or no additional therapy. The tumor was then excised and single cell suspensions were obtained. The T cell infiltration was analyzed by flow cytometry for $CD4^+$ and $CD8^+$ T cells. This approach enabled us to accurately examine the entire tumor mass and reliably quantify the infiltrating lymphocytic population. Sildenafil treatment resulted in a greater $CD8^+$ tumor infiltration. Interestingly, no increase in $CD4^+$ T cells was observed with PDE5 blockade (FIG. 5b insert). Moreover, sildenafil significantly activated the tumor-infiltrating $CD8^+$ T cells as revealed by up-regulation of both CD69 and CD25 activation markers (FIG. 5c). There were no differences in activation markers between the sildenafil-treated group and sildenafil plus adoptive cell therapy (ACT). These data indicate that the anti-tumor efficacy in the sildenafil+ACT group (FIG. 4 and FIG. 5b) is primarily attributable to sildenafil's ability to abrogate the immunosuppressive mechanisms within the tumor microenvironment.

Interestingly, in the advanced tumor setting, the percentage of tumor infiltrating $CD8^+$ T cells negatively correlated (Spearman bivariate correlation $P<0.001$) with tumor size which supports the concept of sildenafil's ability to create a more permissive immune environment (FIG. 5b). The maximal therapeutic effect was seen in the ACT group where a larger $CD8^+$ T cell infiltrate was present in the tumor. Moreover, tetramer staining suggested that the tumor-infiltrating $CD8^+$ more effectively recognized the tumor associated antigen in the sildenafil-treated group. In fact, 9.08%±0.905 of tumor-infiltrating $CD8^+$ cells were specific for AH1, one of the major C26GM-associated antigens, whereas only 1.19±1.180 were tetramer positive in the untreated group (n=3).

IL-2 is required for the activation of naïve T cells and generates a lymphocyte population with heightened recall responses. Furthermore, IL-2 production is associated with the persistence of tumor specific $CD8^+$ lymphocytes within the tumor microenvironment and systemic administration of low doses of IL-2 improves the persistence and antitumor efficacy of transferred T cells (30). It was previously shown that NO can alter IL-2 production in activated lymphocytes. To examine whether the immunomodulatory effect of PDE5 inhibition affected T cell activation within the tumor microenvironment, IL-2 production by TIL was examined. To accomplish this, a transgenic mouse model of green fluorescent protein (GFP) under an IL-2 promoter (BALB/c-IL-2p/GFP) (31) was utilized. In this model, T cell stimulation results in activation of the IL-2 and expression of the reporter transgene GFP, easily detectable by flow cytometry. C26GM-primed BALB/c-IL-2p/GFP splenocytes were adoptively transferred to tumor-bearing recipients that were either left untreated or treated with sildenafil for 9 days. Single cell suspensions of the tumor-infiltrating $CD8^+$ were analyzed by FACS for GFP expression. Adoptively transferred, vaccine-primed T cells were activated in the tumor microenvironment only with PDE5 inhibition whereas, in its absence, they were unable to release IL-2, and hence were bona fide anergic T cells (FIG. 5d).

To further prove that these effects were dependent on $CD8^+$ T cells, mice were challenged with C26GM and either: 1) left untreated; 2) given sildenafil; 3) an anti-CD8 depleting antibody; or 4) both. Sildenafil treatment again demonstrated a statistically significant reduction in tumor outgrowth, an effect completely abolished by $CD8^+$ depletion (FIG. 5e). These experiments indicate that the in vivo MSC suppressive pathways limit T cell infiltration, activation and anti-tumor efficacy. Abrogating these suppressive mechanisms via PDE5 inhibition enhances the tumor specific T cell response and generates a measurable anti-tumor response.

T Cell Proliferation is Restored by PDE5 Inhibition in Multiple Myeloma and Head and Neck Cancer Patients.

Figure 6:
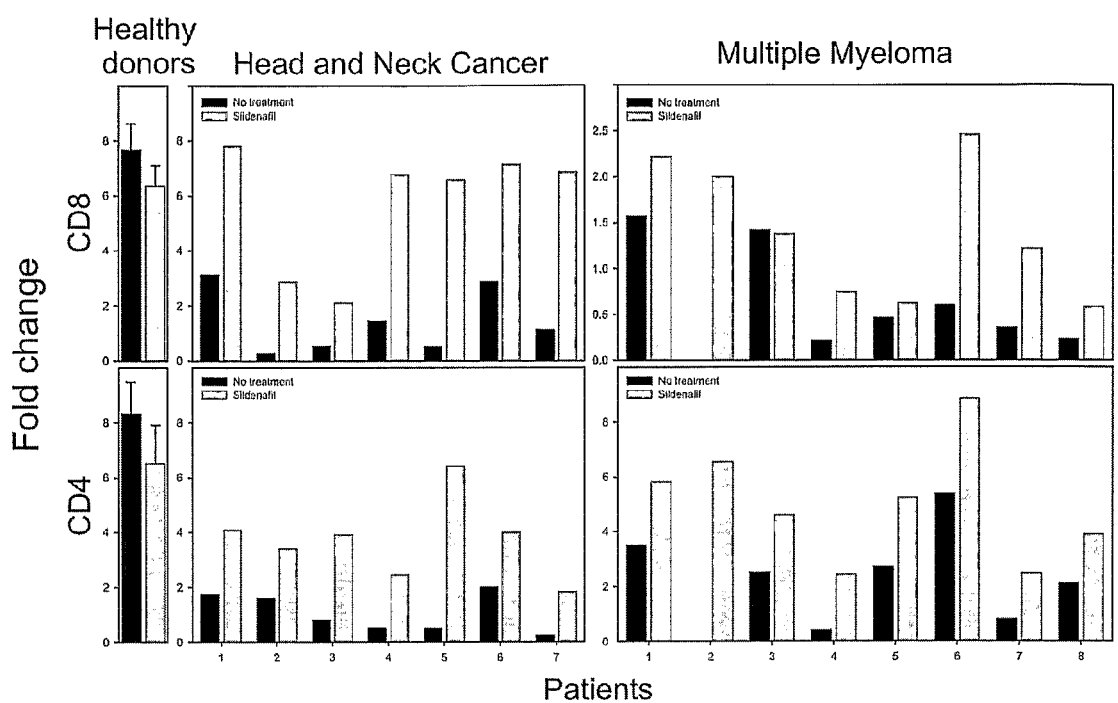
FIG. 6: The impaired lymphocyte proliferation in cancer patients is restored by PDE5 inhibition. Ficoll-purified PBLs from healthy donors, head and neck cancer patients or multiple myeloma patients were stimulated with anti-CD3 and anti-CD28 antibody-coated beads at a 3:1 bead to T cell ratio in the presence or absence of sildenafil (50 μg/ml). CD4$^+$ and CD8$^+$ T cell expansion was measured by flow cytometry 5 days later. Data are reported as fold change calculated as: (number of positive cells in the stimulated culture)/(number of positive cells in the un-stimulated control).

Head and neck cancers express high levels of GM-CSF responsible for the intratumoral infiltration by $CD34^+$ MSC suspected of playing a major role in the immune suppression observed in these patients (32). In fact, it has been shown, that peripheral blood lymphocytes (PBLs) from these patients are functionally impaired in that they fail to be activated and proliferate poorly upon stimulation (33). This anergic state is in large part due to the Arg1 and/or NOS-dependent suppressive activity of MSCs (21, 34). Similar results were also seen in prostate cancer (11) and in multiple myeloma patients (Noonan, unpublished data). It was sought to determine whether one could restore T cell proliferation of PBLs isolated from head and neck and multiple myeloma patients and stimulated with anti-CD3 and anti-CD28 antibody-coated beads, in the presence or absence of sildenafil. While the addition of sildenafil to the culture had no effect on PBLs from healthy donors, PDE5 inhibition significantly restored $CD4^+$ and $CD8^+$ proliferation in all the examined patients (FIG. 6). Interestingly, the addition of sildenafil to isolated $CD3^+$ T cells was unable to increase T cell proliferation (data not shown). Taken together, these human data confirm that the PDE5 inhibition augments immune responsiveness through its effect on an accessory, non-T cell population. Moreover, these data suggest that the same immunosuppressive mechanisms found in mice are conserved in human malignancies and that PDE5 can be a useful therapeutic target to improve anti-tumor immunotherapy.

Cell lines: CT26 and C26-GM are BALB/c colon carcinoma cells lines previously described (10). B16-GM is a C57Bl/6 melanoma cell line previously described (60). Cells were grown in DMEM (Invitrogen Carlsbad, Calif.) or in RPMI medium 1640 (Invitrogen) supplemented with 2 mM L-glutamine/10 mM Hepes/20 µM 2-mercaptoethanol/150 units/ml streptomycin/200 units/ml penicillin/10% heat-inactivated FBS (Harlan, Indianapolis Ind.).

Drugs and Cytokines: Sildenafil (Pfizer, New York N.Y.) was dissolved in the drinking water (20 mg/kg/24 h), given intraperitoneally (ip) daily where indicated (20 mg/kg/24 h) or added to the cell cultures at a final concentration of 50 mg/ml. Tadalafil (Lilly ICOS. Bothel Wash.) was given ip at a concentration of 2 mg/kg/24 h. IFN-γ (25 ng/ml)(Peprotech, Rocky Hill, N.J.) was added where indicated.

Mice and in vivo experiments: 4-6 weeks old Balb/c mice were purchased from Harlan. C57Bl/6-NOS2$^{-/-}$ mice (strain B6; 129P2-Nos2$^{tm1Lau}$) or the control mice (strain B6129 PF2/J 100903) were purchased by Jackson Laboratories (Bar Harbor, Me.). Rag−/− were bred in the Johns Hopkins animal facility. Balb/c-pIL2-GFP mice were a kind gift of CT. Weaver (University of Alabama)(31). pCL4-TCR mice are transgenic for an influenza virus HA512-520 peptide-specific, H-2 Kd-restricted TCR composed of V10 and Vβ8.2 chains were described before (23). All experiments involving the use of mice were in accordance with protocols approved by the Animal Care and Use Committee of the Johns Hopkins University School of Medicine. Tumor measurements were performed in a blind fashion with a caliper by measuring the two main diameters and tumor size is expressed as their product. Mice were euthanized for ethical reasons when tumor size was greater than 150 mm². GR1 depletion was performed by ip injection of 100 μg of anti-GR-1 depleting antibody (clone RB6.8C5-18). This clone was obtained by sub-cloning the originally described RB6.8C5 to maximize the antibody production. CD8 depletion was performed by ip injection of 200 μg of anti-CD8 depleting antibody (clone 2.43) on days 0, 2, 4, 6. The antibodies were produced in vitro in protein-free medium (Invitrogen), purified by G-protein affinity chromatography, and quantified utilizing a Rat IgG2b ELISA (Bethyl Inc Montgomery, Tex.). Adoptive cell transfer (ACT): Donor mice were tumor primed by subcutaneous (sc) injection of $10^6$ γ-irradiated C26GM into four limbs one week prior to adoptive T cell transfer. For the adoptive transfer experiments, lymph nodes and spleens were harvested and mechanically disrupted to obtain single cell suspensions. The cells then underwent RBC lysis with ACK Lysing buffer (Biosource, Camarillo Calif.) and $20 \times 10^6$ cells were injected i.v. into each recipient.

Collagenase treatment of tumors: Single cell suspensions were obtained from the tumors by collagenase treatment. Briefly, tumors were surgically removed, and incubated 30 min @ 37 C.° with a solution of collagenase (10 mg/ml Collagenase, 0.1 mM MgCl2 0.1 mM $CaCl_2$) coupled with mechanical disruption. The reaction was stopped with 10 vol. of medium containing 10% fetal calf serum. The cells were washed, red blood cells lysed, and the cell suspensions were passed through a cell strainer. For hematoxylin-eosin staining, whole tumors were washed twice with PBS and then incubated for 5 days with 10 volumes of 10% neutral buffered formalin.

Flow cytometry: Single cells suspensions from spleens or tumors were stained with Phycoerythrin (PE)-conjugated anti-mouse CD8 (CD8-PE) (BD-Pharmingen San Jose, Calif.), Allophycocyanin (APC)-conjugated anti-mouse CD4 (CD4-APC) (BD-Pharmingen) or with APC conjugated anti-mouse CD11b (BD) and PE-conjugated anti-mouse Gr-1 (CD8-PE). IL4Rα expression was evaluated on purified CD11b⁺ cells by the use of an anti-mouse CD124 PE-conjugated (BD-Pharmingen). Isotyped matched antibodies were used as controls and living cells were gate based on 7AAD, annexinV staining. A total of 100,000 events were collected for each sample on a FACScalibur (BD) flow cytometer, and the data were analyzed using FCS express v2.0 (De-novo software).

Cell purification: CD11b⁺ purification was performed with the Mouse CD11b MicroBeads (Miltenyi Biotec, Bergish-Gladbach, Germany), positive and negative fractions were sorted with the LS columns following the manufacturer's instructions.

Suppressive assay: Purified splenic CD11b⁺ cells ($2 \times 10^5$) were added to CFSE-labeled splenocytes ($10^6$) derived from C14 transgenic mice stimulated for 3 days with Class I $HA_{512-520}$ peptide (IYSTVASSL) in 96 flat bottomed plates. Sildenafil was added where indicated. Proliferation assay: PBLs were obtained from head and neck or multiple myeloma cancer patients having obtained informed consent using an Institutional Review Board-approved protocol. T-cell stimulation was performed by adding anti-CD3/CD28 antibody coated Dynal beads to ficolled PBLs suspended in serum free media at a 3:1 bead to T-cell ratio. The cells were cultured for 5 days in a 96 round-bottom well plate at 37 C 5% CO2. The cells were then labeled with CD4 and CD8 antibodies and analyzed by flow cytometry. Sildenafil was added where indicated. Results are reported as fold change (number of activated cells/number of unactivated cells).

cGMP was measured on purified CD11b⁺ cells using the "Cyclic GMP EIA" Kit (Cayman Chemical Ann Arbor, Mich.). Data analysis was performed with the workbooks available at http://www.caymanchem.com/neptune/servlet/neptune/template/analysis%2CEIA.vm/a/z. Data are expressed as mean +/−SE of quadruplicate wells.

Western Blot: Cells ($10^6$) were purified and washed twice with PBS, and the pellet was resuspended in PBS with 0.2% Triton X-100 and 2 mM EDTA, and incubated for 10 min at room temperature. Cell lysates were centrifuged at 14,000 rpm for 1 min, and 1 vol of Laemmli's sample buffer (4% SDS, 20% glycerol, 10% 2-ME, 4 mg/100 ml bromophenol blue, and 125 mM Tris-HCl; pH 6.8) was added to the supernatant. After incubation at 95° C. for 10 min, lysates were subjected to SDS-PAGE, and proteins were transferred overnight to PVDF membranes. The membranes were saturated at RT in PBS/0.05% Tween 20 containing 2% nonfat milk (Sigma-Aldrich) for 1 hr. The membranes were then incubated overnight at room temperature with rabbit polyclonal anti-NOS2 (Santa Cruz Biotechnology Santa Cruz, Calif.), mouse anti-Arg1 (a kind gift from Augusto C. Ochoa, Lousiana State University, New Orleans, La.) or polyclonal rabbit anti-actin antibody (Sigma-Aldrich), washed twice with PBS/0.05% Tween 20, and incubated with the either mouse anti-mouse IGG or donkey anti rabbit IGG HRP-linked secondary antibody (Amersham Biosciences, Little Chalfont, U.K.) for 1 h at room temperature. Proteins were detected using the Supersignal West picochemiluminescent substrate kit (Pierce, Rockford, Ill.) according to the manufacturer's instructions.

NO measurement: NO was measured using a nitrate/nitrite assay kit (Cayman) according to the manufacturer's instructions. Results were normalized to $10^6$ cells. Data are from triplicate wells.

Arginase assay: CD11b⁺ cells were magnetically purified from the surgically removed tumor, washed twice in PBS-BSA 1%, counted and lysed with Triton X100, 0.1%. The arginase assay was performed as previously described (10).

Statistical analysis: Bivariate Pearson and ANOVA analysis were performed using SPSS v7.0 All experiments were repeated at least twice and all the P values were two-sided (T test) or one-sided (Anova).

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

1. Pardoll, D. 2003. Does the immune system see tumors as foreign or self? *Annu Rev Immunol* 21:807-839.
2. Shankaran, V., Ikeda, H., Bruce, A. T., White, J. M., Swanson, P. E., Old, L. J., and Schreiber, R. D. 2001. IFNgamma and lymphocytes prevent primary tumour development and shape tumour immunogenicity. *Nature* 410:1107-1111.
3. Kaplan, D. H., Shankaran, V., Dighe, A. S., Stockert, E., Aguet, M., Old, L. J., and Schreiber, R. D. 1998. Demonstration of an interferon gamma-dependent tumor surveillance system in immunocompetent mice. *Proc Natl Acad Sci USA* 95:7556-7561.
4. Mocellin, S., Mandruzzato, S., Bronte, V., Lise, M., and Nitti, D. 2004. Part I: Vaccines for solid tumours. *Lancet Oncol* 5:681-689.
5. Rosenberg, S. A., Yang, J. C., and Restifo, N. P. 2004. Cancer immunotherapy: moving beyond current vaccines. *Nat Med* 10:909-915.
6. Gabrilovich, D. 2004. Mechanisms and functional significance of tumour-induced dendritic-cell defects. *Nat Rev Immunol* 4:941-952.
7. Serafini, P., De Santo, C., Marigo, I., Cingarlini, S., Dolcetti, L., Gallina, G., Zanovello, P., and Bronte, V. 2004. Derangement of immune responses by myeloid suppressor cells. *Cancer Immunol Immunother* 53:64-72.
8. Terabe, M., Matsui, S., Park, J. M., Mamura, M., Noben-Trauth, N., Donaldson, D. D., Chen, W., Wahl, S. M., Ledbetter, S., Pratt, B., et al. 2003. Transforming growth factor-beta production and myeloid cells are an effector mechanism through which CD1d-restricted T cells block cytotoxic T lymphocyte-mediated tumor immunosurveillance: abrogation prevents tumor recurrence. *J Exp Med* 198:1741-1752.
9. Bronte, V., Wang, M., Overwijk, W. W., Surman, D. R., Pericle, F., Rosenberg, S. A., and Restifo, N. P. 1998. Apoptotic death of CD8+ T lymphocytes after immunization: induction of a suppressive population of Mac-1+/Gr-1+ cells. *J Immunol* 161:5313-5320.
10. Bronte, V., Serafini, P., De Santo, C., Mango, I., Tosello, V., Mazzoni, A., Segal, D. M., Staib, C., Lowel, M., Sutter, G., et al. 2003. IL-4-induced arginase 1 suppresses alloreactive T cells in tumor-bearing mice. *J Immunol* 170:270-278.
11. Bronte, V., Kasic, T., Gri, G., Gallana, K., Borsellino, G., Marigo, I., Battistini, L., Iafrate, M., Prayer-Galetti, T., Pagano, F., et al. 2005. Boosting antitumor responses of T lymphocytes infiltrating human prostate cancers. *J Exp Med* 201:1257-1268.
12. Bronte, V., Serafini, P., Mazzoni, A., Segal, D. M., and Zanovello, P. 2003. L-arginine metabolism in myeloid cells controls T-lymphocyte functions. *Trends Immunol* 24:302-306.
13. De Santo, C., Serafini, P., Marigo, I., Dolcetti, L., Bolla, M., Del Soldato, P., Melani, C., Guiducci, C., Colombo, M. P., Iezzi, M., et al. 2005. Nitroaspirin corrects immune dysfunction in tumor-bearing hosts and promotes tumor eradication by cancer vaccination. *Proc Natl Acad Sci USA* 102:4185-4190.
14. Perez-Sala, D., Cernuda-Morollon, E., Diaz-Cazorla, M., Rodriguez-Pascual, F., and Lamas, S. 2001. Posttranscriptional regulation of human iNOS by the NO/cGMP pathway. *Am J Physiol Renal Physiol* 280:F466-473.
15. Kiemer, A. K., and Vollmar, A. M. 1998. Autocrine regulation of inducible nitric-oxide synthase in macrophages by atrial natriuretic peptide. *J Biol Chem* 273:13444-13451.
16. Setter, S. M., Iltz, J. L., Fincham, J. E., Campbell, R. K., and Baker, D. E. 2005. Phosphodiesterase 5 inhibitors for erectile dysfunction. *Ann Pharmacother* 39:1286-1295.
17. Lee, A. J., Chiao, T. B., and Tsang, M. P. 2005. Sildenafil for pulmonary hypertension. *Ann Pharmacother* 39:869-884.
18. Takimoto, E., Champion, H. C., Li, M., Belardi, D., Ren, S., Rodriguez, E. R., Bedja, D., Gabrielson, K. L., Wang, Y., and Kass, D. A. 2005. Chronic inhibition of cyclic GMP phosphodiesterase 5A prevents and reverses cardiac hypertrophy. *Nat Med* 11:214-222.
19. Pauleau, A. L., Rutschman, R., Lang, R., Perris, A., Watowich, S. S., and Murray, P. J. 2004. Enhancer-mediated control of macrophage-specific arginase I expression. *J Immunol* 172:7565-7573.
20. Mazzoni, A., Bronte, V., Visintin, A., Spitzer, J. H., Apolloni, E., Serafini, P., Zanovello, P., and Segal, D. M. 2002. Myeloid suppressor lines inhibit T cell responses by an NO-dependent mechanism. *J Immunol* 168:689-695.
21. Rodriguez, P. C., Quiceno, D. G., Zabaleta, J., Ortiz, B., Zea, A. H., Piazuelo, M. B., Delgado, A., Correa, P., Brayer, J., Sotomayor, E. M., et al. 2004. Arginase I production in the tumor microenvironment by mature myeloid cells inhibits T-cell receptor expression and antigen-specific T-cell responses. *Cancer Res* 64:5839-5849.
22. Bronte, V., Chappell, D. B., Apolloni, E., Cabrelle, A., Wang, M., Hwu, P., and Restifo, N. P. 1999. Unopposed production of granulocyte-macrophage colony-stimulating factor by tumors inhibits CD8+ T cell responses by dysregulating antigen-presenting cell maturation. *J Immunol* 162:5728-5737.
23. Serafini, P., Carbley, R., Noonan, K. A., Tan, G., Bronte, V., and Borrello, I. 2004. High-dose granulocyte-macrophage colony-stimulating factor-producing vaccines impair the immune response through the recruitment of myeloid suppressor cells. *Cancer Res* 64:6337-6343.
24. Dudley, M. E., and Rosenberg, S. A. 2003. Adoptive-cell-transfer therapy for the treatment of patients with cancer. *Nat Rev Cancer* 3:666-675.
25. Zhang, L., Conejo-Garcia, J. R., Katsaros, D., Gimotty, P. A., Massobrio, M., Regnani, G., Makrigiannakis, A., Gray, H., Schlienger, K., Liebman, M. N., et al. 2003. Intratumoral T cells, recurrence, and survival in epithelial ovarian cancer. *N Engl J Med* 348:203-213.
26. Mihm, M. C., Jr., Clemente, C. G., and Cascinelli, N. 1996. Tumor infiltrating lymphocytes in lymph node melanoma metastases: a histopathologic prognostic indicator and an expression of local immune response. *Lab Invest* 74:43-47.
27. Naito, Y., Saito, K., Shiiba, K., Ohuchi, A., Saigenji, K., Nagura, H., and Ohtani, H. 1998. CD8+ T cells infiltrated within cancer cell nests as a prognostic factor in human colorectal cancer. *Cancer Res* 58:3491-3494.
28. Schumacher, K., Haensch, W., Roefzaad, C., and Schlag, P. M. 2001. Prognostic significance of activated CD8(+) T cell infiltrations within esophageal carcinomas. *Cancer Res* 61:3932-3936.
29. Vesalainen, S., Lipponen, P., Tali a, M., and Syrjanen, K. 1994. Histological grade, perineural infiltration, tumour-infiltrating lymphocytes and apoptosis as determinants of long-term prognosis in prostatic adenocarcinoma. *Eur J Cancer* 30A:1797-1803.

30. Yee, C., Thompson, J. A., Byrd, D., Riddell, S. R., Roche, P., Celis, E., and Greenberg, P. D. 2002. Adoptive T cell therapy using antigen-specific CD8+ T cell clones for the treatment of patients with metastatic melanoma: in vivo persistence, migration, and antitumor effect of transferred T cells. *Proc Natl Acad Sci USA* 99:16168-16173.

31. Saparov, A., Wagner, F. H., Zheng, R., Oliver, J. R., Maeda, H., Hockett, R. D., and Weaver, C. T. 1999. Interleukin-2 expression by a subpopulation of primary T cells is linked to enhanced memory/effector function. *Immunity* 11:271-280.

32. Pak, A. S., Wright, M. A., Matthews, J. P., Collins, S. L., Petruzzelli, G. J., and Young, M. R. I. 1995. Mechanisms of immune suppression in patients with head and neck cancer: presence of CD34(+) cells which suppress immune functions within cancers that secrete granulocyte-macrophage colony-stimulating factor. *Clin Cancer Res* 1:95-103.

33. Young, M. R., Wright, M. A., and Pandit, R. 1997. Myeloid differentiation treatment to diminish the presence of immune-suppressive CD34+ cells within human head and neck squamous cell carcinomas. *J Immunol* 159:990-996.

34. Xu, W., Liu, L. Z., Loizidou, M., Ahmed, M., and Charles, I. G. 2002. The role of nitric oxide in cancer. *Cell Res* 12:311-320.

35. Zhao, L., Mason, N. A., Morrell, N. W., Kojonazarov, B., Sadykov, A., Maripov, A., Mirrakhimov, M. M., Aldashev, A., and Wilkins, M. R. 2001. Sildenafil inhibits hypoxia-induced pulmonary hypertension. *Circulation* 104:424-428.

36. Ghofrani, H. A., Wiedemann, R., Rose, F., Schermuly, R. T., Olschewski, H., Weissmann, N., Gunther, A., Walmrath, D., Seeger, W., and Grimminger, F. 2002. Sildenafil for treatment of lung fibrosis and pulmonary hypertension: a randomised controlled trial. *Lancet* 360:895-900.

37. Lechner, M., Lirk, P., and Rieder, J. 2005. Inducible nitric oxide synthase (iNOS) in tumor biology: The two sides of the same coin. *Semin Cancer Biol.*

38. Ambs, S., Merriam, W. G., Ogunfusika, M. O., Bennett, W. P., Ishibe, N., Hussain, S. P., Tzeng, E. E., Geller, D. A., Billiar, T. R., and Harris, C. C. 1998. p53 and vascular endothelial growth factor regulate tumor growth of NOS2-expressing human carcinoma cells. *Nat Med* 4:1371-1376.

39. Vousden, K. H., and Prives, C. 2005. P53 and prognosis: new insights and further complexity. *Cell* 120:7-10.

40. Hussain, S. P., Hofseth, L. J., and Harris, C. C. 2003. Radical causes of cancer. *Nat Rev Cancer* 3:276-285.

41. Morbidelli, L., Donnini, S., and Ziche, M. 2004. Role of nitric oxide in tumor angiogenesis. *Cancer Treat Res* 117:155-167.

42. Zou, W. 2005 Immunosuppressive networks in the tumour environment and their therapeutic relevance. *Nat Rev Cancer* 5:263-274.

43. Hoffman, R. A., Mahidhara, R. S., Wolf-Johnston, A. S., Lu, L., Thomson, A. W., and Simmons, R. L. 2002. Differential modulation of CD4 and CD8 T-cell proliferation by induction of nitric oxide synthesis in antigen presenting cells. *Transplantation* 74:836-845.

44. Baniyash, M. 2004. TCR zeta-chain downregulation: curtailing an excessive inflammatory immune response. *Nat Rev Immunol* 4:675-687.

45. Bronte, V., and Zanovello, P. 2005. Regulation of immune responses by L-arginine metabolism. *Nat Rev Immunol* 5:641-654.

46. Liu, Y., Christou, H., Morita, T., Laughner, E., Semenza, G. L., and Kourembanas, S. 1998. Carbon monoxide and nitric oxide suppress the hypoxic induction of vascular endothelial growth factor gene via the 5' enhancer. *J Biol Chem* 273:15257-15262.

47. Pilz, R. B., and Casteel, D. E. 2003. Regulation of gene expression by cyclic GMP. *Circ Res* 93:1034-1046.

48. Kloss, S., Fumeaux, H., and Mulsch, A. 2003. Post-transcriptional regulation of soluble guanylyl cyclase expression in rat aorta. *J Biol Chem* 278:2377-2383.

49. Rotella, D. P. 2002. Phosphodiesterase 5 inhibitors: current status and potential applications. *Nat Rev Drug Discov* 1:674-682.

50. Webb, B. L., Hirst, S. J., and Giembycz, M. A. 2000. Protein kinase C isoenzymes: a review of their structure, regulation and role in regulating airways smooth muscle tone and mitogenesis. *Br J Pharmacol* 130:1433-1452.

51. Vellenga, E., Dokter, W., and Halie, R. M. 1993. Interleukin-4 and its receptor; modulating effects on immature and mature hematopoietic cells. *Leukemia* 7:1131-1141.

52. Gorelik, L., and Flavell, R. A. 2001 Immune-mediated eradication of tumors through the blockade of transforming growth factor-beta signaling in T cells. *Nat Med* 7:1118-1122.

53. Zippelius, A., Batard, P., Rubio-Godoy, V., Bioley, G., Lienard, D., Lejeune, F., Rimoldi, D., Guillaume, P., Meidenbauer, N., Mackensen, A., et al. 2004. Effector function of human tumor-specific CD8 T cells in melanoma lesions: a state of local functional tolerance. *Cancer Res* 64:2865-2873.

54. Curiel, T. J., Coukos, G., Zou, L., Alvarez, X., Cheng, P., Mottram, P., Evdemon-Hogan, M., Conejo-Garcia, J. R., Zhang, L., Burow, M., et al. 2004. Specific recruitment of regulatory T cells in ovarian carcinoma fosters immune privilege and predicts reduced survival. *Nat Med* 10:942-949.

55. Lathers, D. M., Achille, N., Kolesiak, K., Hulett, K., Sparano, A., Petruzzelli, G. J., and Young, M. R. 2001. Increased levels of immune inhibitory CD34+ progenitor cells in the peripheral blood of patients with node positive head and neck squamous cell carcinomas and the ability of these CD34+ cells to differentiate into immune stimulatory dendritic cells. *Otolaryngol Head Neck Surg* 125:205-212.

56. Noonan, K., Matsui, W., Serafini, P., Carbley, R., Tan, G., Khalili, J., Bonyhadi, M., Levitsky, H., Whartenby, K., and Borrello, I. 2005. Activated marrow-infiltrating lymphocytes effectively target plasma cells and their clonogenic precursors. *Cancer Res* 65:2026-2034.

57. Serafini, P., Borrello, I., and Bronte, V. 2005. Myeloid suppressor cells in cancer: Recruitment, phenotype, properties, and mechanisms of immune suppression. *Semin Cancer Biol.*

58. Freeman, B. D., Danner, R. L., Banks, S. M., and Natanson, C. 2001. Safeguarding patients in clinical trials with high mortality rates. *Am J Respir Crit Care Med* 164:190-192.

59. Mocellin, S., Wang, E., and Marincola, F. M. 2001. Cytokines and immune response in the tumor microenvironment. *J Immunother* 24:392-407.

60. Dranoff, G., Jaffee, E., Lazenby, A., Golumbek, P., Levitsky, H., Brose, K., Jackson, V., Hamada, H., Pardoll, D., and Mulligan, R. C. 1993. Vaccination with irradiated tumor cells engineered to secrete murine granulocyte-macrophage colony-stimulating factor stimulates potent, specific, and long-lasting anti-tumor immunity. *Proc Natl Acad Sci USA* 90:3539-3543.

What is claimed is:

1. A method of treating cancer in a human patient having myeloid suppressor cell mediated immunosuppression, comprising:
   administering adoptive cell transfer therapy comprising lymphocytes to the patient; and
   administering a therapeutically effective amount of a phosphodiesterase-5 inhibitor compound to the patient.

2. The method of claim 1, wherein the patient comprises tumor-infiltrating myeloid suppressor cells.

3. The method of claim 1, wherein the phosphodiesterase-5 inhibitor compound is sildenafil, vardenafil, or tadalafil.

4. The method of claim 1, wherein the phosphodiesterase-5 inhibitor compound is administered daily.

5. The method of claim 1, wherein the cancer is multiple myeloma, a lymphoma, melanoma, breast, stomach, head and neck, ovarian, colon, prostate, lung, or cervical cancer.

6. The method of claim 5, wherein the cancer is multiple myeloma or head and neck cancer.

7. The method of claim 5, wherein the cancer is colon cancer.

8. The method of claim 1, wherein the lymphocytes are tumor infiltrating lymphocytes.

9. A method of treating cancer in a human patient, comprising administering to the patient a therapeutically effective amount of a phosphodiesterase-5 inhibitor compound daily, wherein:
   the patient comprises myeloid suppressor cells;
   the myeloid suppressor cells are responsible for immune suppression in the patient;
   the immune suppression is associated with the cancer; and
   the phosphodiesterase-5 inhibitor compound is sildenafil, vardenafil, or tadalafil.

10. The method of claim 9, further comprising administering an anticancer agent to the patient, wherein the anticancer agent is anthracycline, taxane, an alkylating agent, cis-platin, arabinofuranosyl cytosine, 5-fluorouracil, altretamine, busulfan, chlorambucil, cyclophosphamide, ifosfamide, mechlorethamine, melphalan, thiotepa, cladribine, floxuridine, gemcitabine, thioguanine, pentostatin, methotrexate, 6-mercaptopurine, cytarabine, carmustine, lomustine, streptozotocin, carboplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, prednisone, bleomycin, dactinomycin, daunorubicin, doxirubicin, idarubicin, mitoxantrone, losoxantrone, mitomycin-c, plicamycin, paclitaxel, docetaxel, CPI-11, epothilones, topotecan, irinotecan, 9-amino camptothecan, 9-nitro camptothecan, GS-211, etoposide, teniposide, vinblastine, vincristine, vinorelbine, procarbazine, asparaginase, pegaspargase, methoxtrexate, octreotide, estramustine, hydroxyurea, tamoxifen, raloxifene, toremifene, exemestane, letrozole, anastrozole, megestrol, trastuzumab, goserelin acetate, fulvestrant, doxorubicin, epirubicin, or cyclophosphonamide.

11. The method of claim 9, further comprising administering an anticancer vaccine to the patient, wherein the vaccine is a DNA-based vaccine, a protein-based vaccine, a whole cell tumor vaccine, or a dendritic cell-based vaccine.

12. The method of claim 9, wherein the myeloid suppressor cells are tumor-infiltrating myeloid suppressor cells.

13. The method of claim 3, wherein the phosphodiesterase-5 inhibitor compound is tadalafil, and the tadalafil is administered orally at a dose of 5 mg, 10 mg, or 20 mg.

14. The method of claim 13, wherein the tadalafil is administered orally at a dose of 20 mg.

15. The method of claim 3, wherein the phosphodiesterase-5 inhibitor compound is vardenafil, and the vardenafil is administered orally at a dose of 5 mg, 10 mg, or 20 mg.

16. The method of claim 3, wherein the phosphodiesterase-5 inhibitor compound is sildenafil, and the sildenafil is administered orally at a dose of 25 mg, 50 mg, or 100 mg.

* * * * *